United States Patent
Matsuura et al.

(10) Patent No.: US 6,682,473 B1
(45) Date of Patent: Jan. 27, 2004

(54) DEVICES AND METHODS FOR ATTENUATION OF PRESSURE WAVES IN THE BODY

(75) Inventors: David G. Matsuura, Encinitas, CA (US); Walter D. Gillespie, La Mesa, CA (US); Sheila K. Wallin, Irvine, CA (US); Kevin G. Connors, Wellesley, MA (US); Edward Bullister, Newton, MA (US)

(73) Assignee: Solace Therapeutics, Inc., Carlsbad, CA (US)

(*) Notice: Subject to any disclaimer, the term of this patent is extended or adjusted under 35 U.S.C. 154(b) by 0 days.

(21) Appl. No.: 09/723,309

(22) Filed: Nov. 27, 2000

Related U.S. Application Data

(60) Provisional application No. 60/197,095, filed on Apr. 14, 2000.

(51) Int. Cl.[7] .................................................. A61F 2/00
(52) U.S. Cl. ....................................................... 600/29
(58) Field of Search ............................ 600/29, 30, 31, 600/32; 128/898

(56) References Cited

U.S. PATENT DOCUMENTS

| | | |
|---|---|---|
| 3,841,304 A | 10/1974 | Jones |
| 4,246,893 A | 1/1981 | Berson |
| 4,311,146 A | 1/1982 | Wonder |
| 4,341,218 A | 7/1982 | Ü |
| 4,346,712 A | 8/1982 | Handa et al. |
| 4,364,392 A | 12/1982 | Strother et al. |
| 4,416,267 A | 11/1983 | Garren et al. |
| 4,441,495 A | 4/1984 | Hicswa |
| 4,517,979 A | 5/1985 | Pecenka |
| 4,545,367 A | 10/1985 | Tucci |
| 4,607,618 A | 8/1986 | Angelchik |
| 4,694,827 A | 9/1987 | Weiner et al. |
| 4,723,547 A | 2/1988 | Kullas et al. |
| 4,773,393 A | 9/1988 | Haber et al. |
| 4,802,479 A | 2/1989 | Haber et al. |
| 4,819,637 A | 4/1989 | Dormandy, Jr. et al. |
| 4,832,680 A | 5/1989 | Haber et al. |
| 4,850,963 A | 7/1989 | Sparks et al. |
| 4,899,747 A | 2/1990 | Garren et al. |
| 4,925,446 A | 5/1990 | Garay et al. |
| 4,930,535 A | 6/1990 | Rinehold |
| 5,084,061 A | 1/1992 | Gau et al. |
| 5,144,708 A | 9/1992 | Pekar |
| 5,181,921 A | 1/1993 | Makita et al. |

(List continued on next page.)

FOREIGN PATENT DOCUMENTS

| | | |
|---|---|---|
| WO | WO 99/24106 | 5/1999 |
| WO | WO 00/54701 | 9/2000 |
| WO | WO 00/54702 | 9/2000 |

OTHER PUBLICATIONS

*A New Technique for Dynamic Analysis of Bladder Compliance*, Robert F. Gilmore et al., *The Journal of Urology*, vol. 150, pp. 1200–1203, Oct. 1993.

(List continued on next page.)

*Primary Examiner*—Max F. Hindenburg
*Assistant Examiner*—Brian Szmal
(74) *Attorney, Agent, or Firm*—Knobbe, Martens, Olson & Bear, LLP

(57) ABSTRACT

Disclosed are pressure attenuators, for attenuating pressure changes in an anatomical structure. The attenuators are movable from a first, introduction configuration to a second, implanted configuration. When in the second, implanted configuration, the attenuator attenuates pressure spikes within the body by reversibly reducing in volume in response to the pressure spike. In one application, the attenuator is utilized to treat urinary tract dysfunctions. Deployment devices, retrieval devices, and methods are also disclosed.

62 Claims, 29 Drawing Sheets

U.S. PATENT DOCUMENTS

| | | | |
|---|---|---|---|
| 5,222,970 | A | 6/1993 | Reeves |
| 5,248,275 | A | 9/1993 | McGrath et al. |
| 5,304,123 | A | 4/1994 | Atala et al. |
| 5,308,327 | A | 5/1994 | Heaven et al. |
| 5,411,475 | A | 5/1995 | Atala et al. |
| 5,433,216 | A | 7/1995 | Sugrue et al. |
| 5,437,603 | A | 8/1995 | Cerny et al. |
| 5,479,945 | A | 1/1996 | Simon |
| 5,501,669 | A | 3/1996 | Conway et al. |
| 5,564,143 | A | 10/1996 | Pekar et al. |
| 5,603,685 | A | 2/1997 | Tutrone, Jr. |
| 5,617,876 | A | 4/1997 | van Duyl |
| 5,779,672 | A | 7/1998 | Dormandy, Jr. |
| 5,830,228 | A | 11/1998 | Knapp et al. |
| 5,830,780 | A | 11/1998 | Dennison et al. |
| 5,868,141 | A | 2/1999 | Ellias |
| 5,964,806 | A | 10/1999 | Cook et al. |
| 6,021,781 | A * | 2/2000 | Thompson et al. ......... 128/898 |
| 6,045,498 | A | 4/2000 | Burton et al. |
| 6,119,697 | A | 9/2000 | Engel et al. |
| 6,293,923 | B1 | 9/2001 | Yachia et al. |
| 6,398,718 | B1 | 6/2002 | Yachia et al. |
| 2002/0055730 | A1 | 1/2002 | Yachia et al. |
| 2002/0082551 | A1 | 6/2002 | Yachia et al. |
| 2002/0165427 | A1 | 11/2002 | Yachia et al. |

OTHER PUBLICATIONS

*The Effect of Urinary Bladder Shape on its Mechanics During Filling*, Margot S. Damasar et al., *Pergamon*, vol. 6, pp. 725–732, 1995.

*Difference in Bladder Compliance with Time and Associations of Bladder Management with Compliance in Spinal Cord Injured Patients*, Kyle J. Weld et al., *The Journal of Urology*, vol. 163, pp. 1228–1233, Apr. 2000.

*Visco–elastic Properties of Isolated Detrusor Smooth Muscle*, A. Wagg et al., *Scandinavian Journal of Urology Nephoral*, Suppl. 201, pp 12–18, 1999.

*Urge Incontinence and the Unstable Bladder, Practical Urogynecology*, Chapter 8—Incontinence and the Unstable Bladder, pp. 191–214.

*Decreased Elastin Gene Expression in Noncompliant Human Bladder Tissue: A Competitive Reverse Transcriptase–Polymerase Chain Reaction Analysis*, Bob Djavan et al., *Journal of Urology*, vol. 160, pp. 1658–1662, Nov. 1998.

*Molecular, Cellular and Experimental Morphology*, Narinder Dass et al., *Journal of Anatomy*, vol. 195, Part 3, pp. 447–453, Oct. 1999.

*Design of Miniaturized Bladder Volume Monitor and Subsequent Preliminary Evaluation on 41 Enuretic Patients, IEEE Transactions on Rehabilitation Engineering*, vol. 6, No. 1, pp. 66–74, Mar. 1998.

*Temporal Expression of Elastic Fiber Components in Bladder Development*, H.P. Koo et al., *Connective Tissue Research*, vol. 3701–20, pp. 1–11, 1998.

*Voiding Dysfunction in Ileal Neobladder*, Naohito Mikuma et al., *The Journal of Urology*, vol. 158 pp. 1365–1367, Oct. 1997.

*Interstital Cystitus: Bladder Training with Intravesical Oxybutynin*, George A. Barbalias et al., *The Journal of Urology*, vol. 163, pp. 1818–1822, Jun. 2000.

*Noninvasive Evaluation of Bladder Compliance in Children Using Ultrasound Estimated Bladder Weight*, Osamu Ukimura et al., *The Journal of Urology*, vol. 160 pp. 1459–1462, Oct. 1998.

*Surgical Complications of Bladder Augmentation: Comparison Between Various Enterocystoplasties in 133 Patients*, Bijan Shekarriz et al., *Elsevier Science Inc.*, Pediatric Urology 55, pp. 123–128, 2000.

*Elastic Fibers and Their Role in Bladder Extracellular Matrix*, Joel Rosenbloom et al., *Muscle, Matrix and Bladder Function*, vol. 385, pp. 161–184, 1995.

*Effect of Spinal Versus General Anesthesia on Bladder Compliance and Intraabdominal Pressure During Transurethral Procedures*, David Olsfanger et al., *Journal of Clinical Anesthesia*, vol. 11, pp. 328–331, 1999.

*Structure of the Lymphatic Microcirculation in the Human Urinary Bladder with Different Intraluminal Pressure and Distension*, R. Scelsi et al., *Lymphology*, pp. 60–66, 1996.

*Boston Scientific Target Detachable Silicone Balloon*, Product Information, Part No.: ES–05827 Rev. A.

Abstract, *Surgical treatment for stress urinary incontinence associated with valsalva induced detrusor instability.*, S. R. Serels et al. *Website PubMed*.

Abstract, *Identifying patients who require urodynamic testing before surgery for stress incontinence based on questionnaire information and surgical history.*, G. E. Lemack et al., *Website PubMed*.

Abstract, *Ambulatory urodynamics: do they help clinical mamagement?*, E. Gorton et al., *Website PubMed*.

Abstract, *The effect of bladder filling on changes in ultrasonography parameters of the lower urinary tract in women with urinary stress incontinence.*, A. Martan et al., *Website PubMed*.

Abstract, *Urodynamic protocol and central review of data for clinical trials in lower urinary tract dysfunction.*, P. Lewis et al., *Website PubMed*.

Abstract, *New data on the diagnosis and treatment of urinary stress incontinence in women.*, J. Colin et al., *Website PubMed*.

Abstract, *Office evaluation of the patient with an overactive bladder.*, J. J. Kowalczyk, *Website PubMed*.

Abstract, *Surgical and medical treatment options for urge incontinence.*, J. M. Lonsway, *Website PubMed*.

Abstract, *Experimental development of a fixed volume, gravity draining, prosthetic urinary bladder.*, M.J. Gleeson et al., *Website PubMed*.

Abstract, *Urodynamics of normal and disordered miction.*, U. Jonas, *Website PubMed*.

Abstract, *Whole bladder mechanics during filling.*, M. S. Damaser, *Website PubMed*.

Abstract, *A mathematical micturition to restore simple flow recordings in healthy and symptomatic individuals and enhance uroflow interpretation.*, F. A. Valentini et al., *Website PubMed*.

Abstract, *Barometers and bladders: a primer on pressures.*, D. A. Bloom et al., *Website PubMed*.

*Die Detrusormyektomie (Autoaugmentation) in der Dehandlung der Hyperreflexiven Low–compliance–Blasé*, M. Stohrer et al., *Der Urologe [A]*, pp. 30–37, 1999.

*Effect of aging on bladder function and the response to outlet obstruction in female rats*, A.D. Kohan et al., *Urol Res*, 2000, 28: pp. 33–37.

* cited by examiner

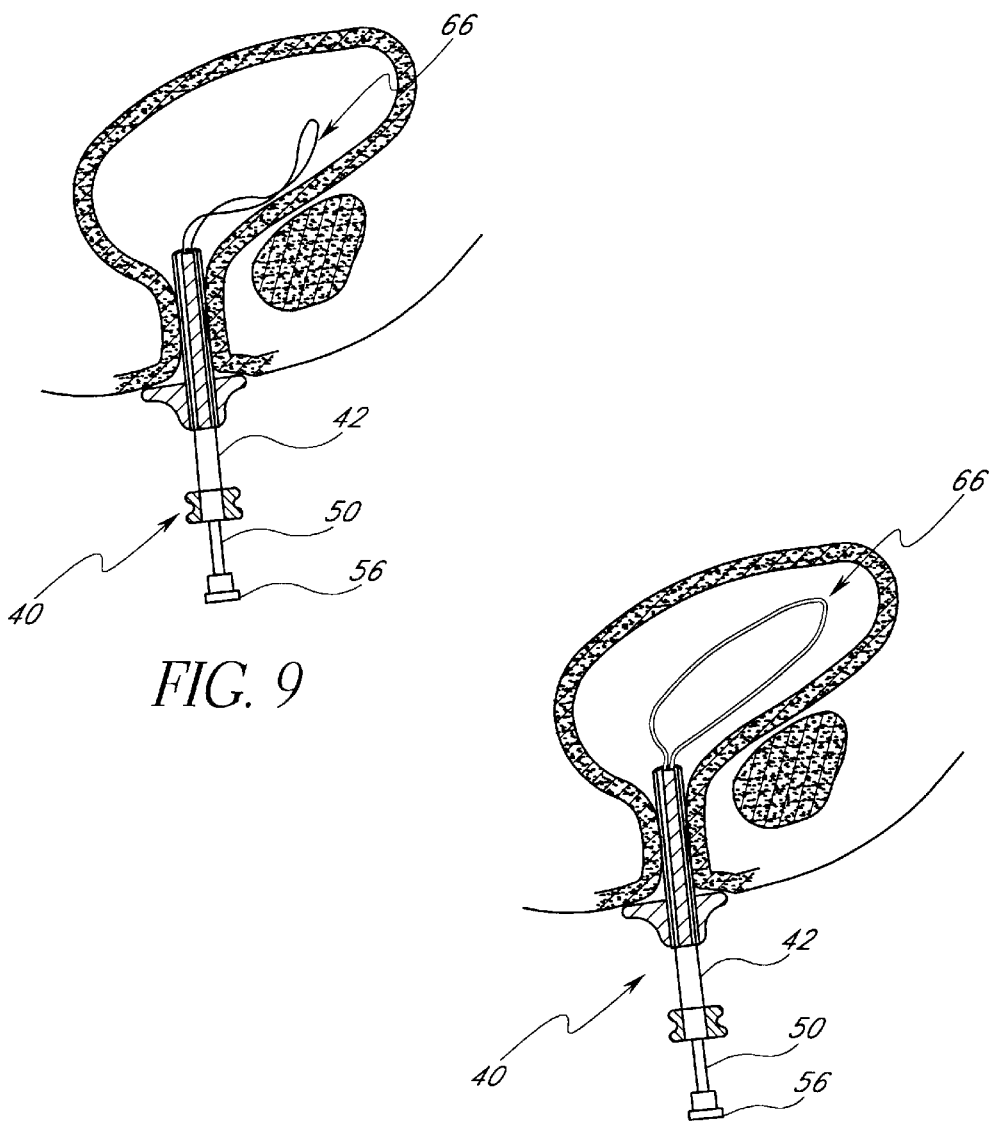

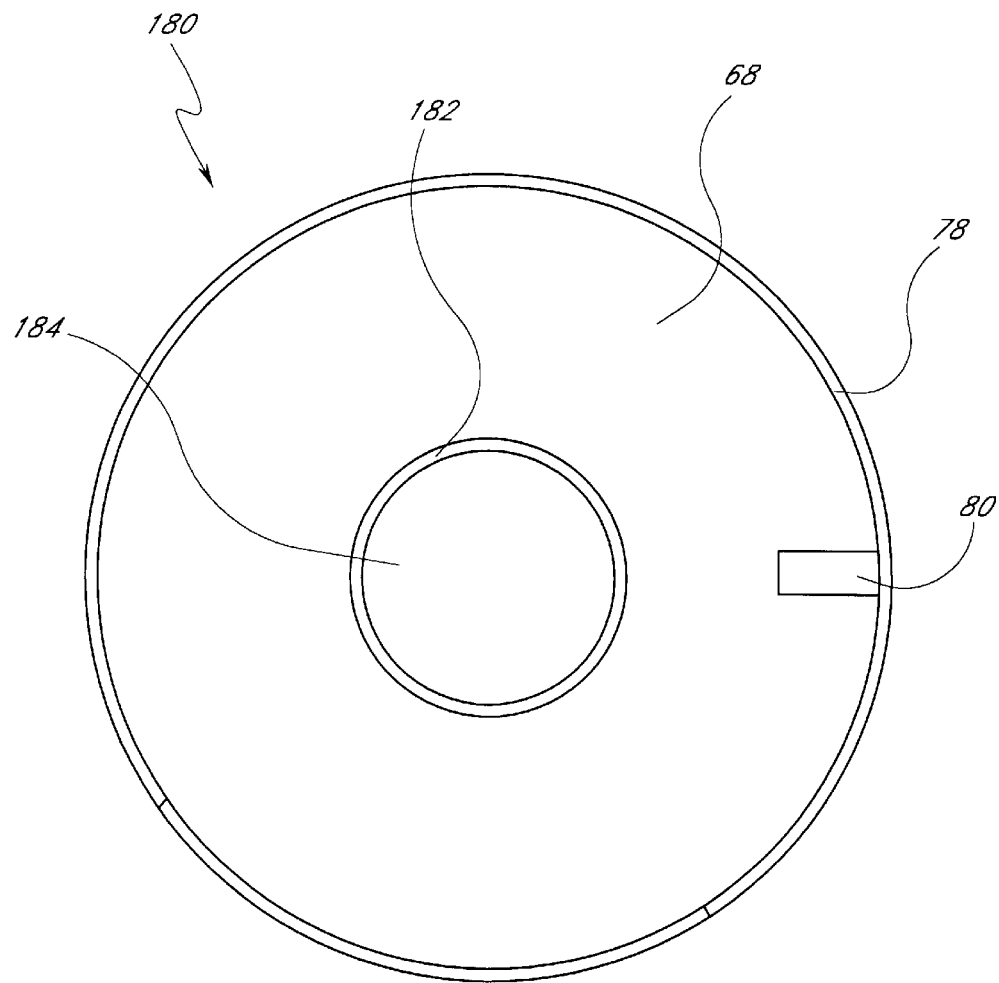
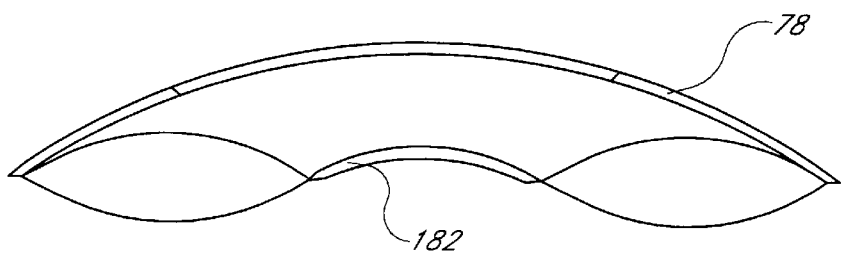
FIG. 13

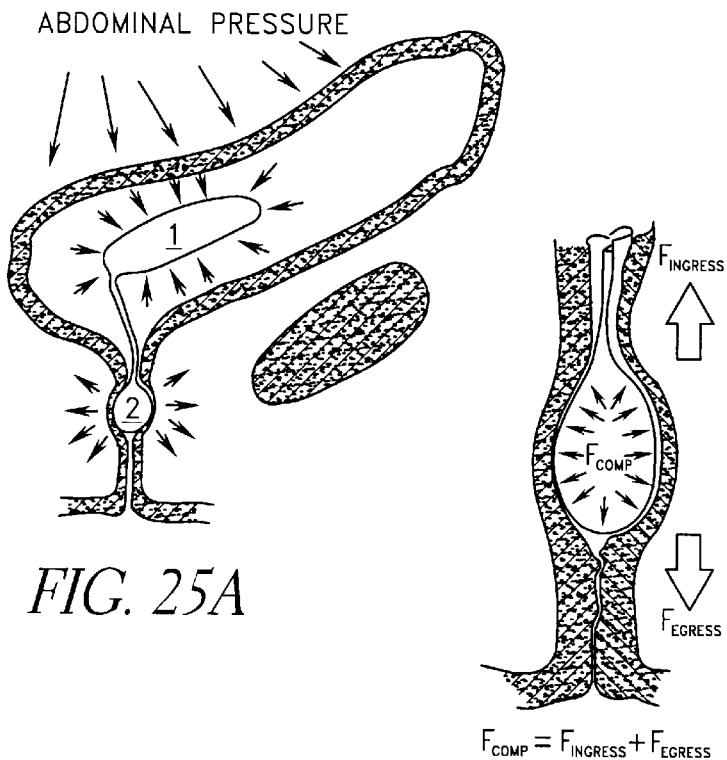
FIG. 25A
FIG. 25B
$F_{COMP} = F_{INGRESS} + F_{EGRESS}$
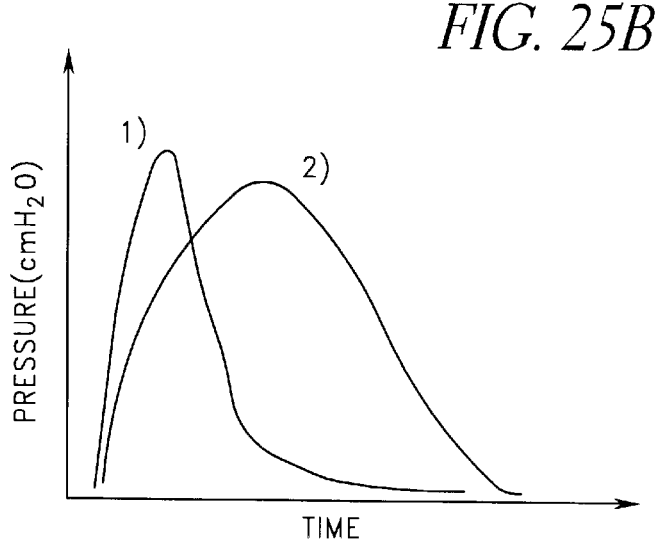
1) INTRA-VESSICAL PRESSURE: RAPID RISE TIME, RAPID DECAY...
2) SECONDARY BALLOON PRESSURE: RAPID RISE TIME, DELAYED DECAY TIME...
FIG. 25C

DEVICES AND METHODS FOR ATTENUATION OF PRESSURE WAVES IN THE BODY

This application claims priority to U.S. Provisional Patent Application Ser. No. 60/197,095, filed Apr. 14, 2000, the disclosure of which is incorporated in its entirety herein by reference.

BACKGROUND OF THE INVENTION

1. Field of the Invention

The present invention relates generally to methods and apparatus for attenuating and/or baffling transient pressure waves in relatively incompressible materials in organs of the body, including, but not limited to the following systems of the human body: cardiovascular, pulmonary, renal/urological, gastrointestinal, hepatic/biliary, gynecological, central nervous, musculoskeletal, otorhinolaryngical and ophthalmic.

In one particular aspect, the present invention relates generally to the field of urology and gynecology, and in particular to the treatment of disorders of the urinary tract caused by sudden fluctuations of intravesical pressure. More specifically, in this aspect of the present invention, methods and devices are provided for the diagnosis and treatment of urinary disorders such as incontinence, urgency, frequency, interstitial cystitis, irritable bladder syndrome and neurogenic bladders.

2. Description of the Related Art

Pressure waves are known to propagate through incompressible fluids in various organs of the body. These pressure waves may be caused by a number of events including events within the body, such as a beating heart, breathing in the lungs, peristalsis actions in the GI tract, movement of the muscles of the body, or external events such as coughing, laughing, external trauma to the body, and movement of the body relative to gravity. As the elasticity of the surrounding tissues and organs, sometimes referred to as compliance, decreases, the propagation of these pressure waves increases. These pressure waves have many undesirable effects ranging from discomfort, to stress on the organs and tissue, to fluid leakage such as urinary incontinence, to renal failure, stroke, heart attack and blindness. accumulators and wave diffusers are types of devices that can modulate pressure waves in various nonanalogous settings. Accumulator technology is well known and used in hydraulic systems in aircraft, manufacturing equipment, and water supply and distribution since the 1940's. Common types of accumulators include bladder accumulators, piston accumulators, non-separator (air over fluid), and weight loaded type accumulators.

Wave diffusers also affect the transmission of pressure waves in incompressible systems in various settings. The function of such diffusers is to interrupt the progress of a pressure wave and distribute the energy of the wave in so many directions so as to destroy the integrity of a uniform wavefront and its resultant effects. Wave diffusers may be used to protect a specified area from the impact of a wavefront.

Urinary tract disorders are a widespread problem in the U.S. and throughout the world, affecting people of all ages both physiologically and psychologically. Urinary tract disorders have a number of causes including birth defects, disease, injury, aging, and urinary tract infection.

In light of the foregoing, a number of attempts have been made to combat these disorders. One such attempt involves the use of an indwelling catheter connected to a collection bag with a clamping device on the catheter. Indwelling catheters, however, have a number of drawbacks. For instance, there is an infection risk associated with indwelling catheters, which provide a direct passage for bacteria or other microorganisms into the bladder. Thus, indwelling catheters can only be used for relatively short-term situations. In addition, indwelling catheters and associated collection bags are not cosmetically appealing to most patients.

An attempt at solving urinary incontinence involves the use of prosthetic urethral valves. One such prior art valve utilizes an inflatable cuff that is inserted around the outside of the urethra. The urethral valves of the prior art also have numerous disadvantages. One disadvantage of these valves is that they typically require surgery for installation, and some prior art valves must be operated externally and are therefore dependent on manual intervention.

The use of intra-urethral valves is also known. Typical intra-urethral valves of the prior art also generally require manual intervention. Another problem associated with prior art intra-urethral valves is that the valves may be displaced into the bladder or expelled from the urethra. There is also an infection risk associated with many such valves since they often extend into the meatus and/or have portions of the device external to the urethra providing a passage for microorganisms into the bladder.

Electrical stimulation therapy including rectal, intravaginal and external has been attempted to tone the muscles and stimulate nerves supporting the bladder and urethra. This therapy requires lengthy and numerous treatments, and any benefits derived from the therapy typically diminish when the treatments are stopped.

Current surgical incontinence procedures typically focus on the augmentation of urethral flow resistance. Prior art surgical interventions include bladder neck suspensions and bulk (collagen) injections. Although these procedures can be clinically effective with certain patients, problems include widely variable clinical outcomes, relative high costs to perform, potential complications related to surgery, and any effects may be short lived.

Drug therapy exists for a number of urinary tract conditions, including overactive bladder. These drugs include oral medications (systemic) and drugs delivered directly into the bladder. These drugs typically suffer from side effects, lack of effectiveness and high morbidity. Oral medications typically do not allow immediate relief of symptoms and include side effects such as dry mouth and constipation. Drugs delivered directly into the bladder often require continuous or intermittent catheterization for introduction of the therapeutic at the clinically appropriate time.

The intent of the treatment methods described to date either focus on the augmentation of urethral flow resistance, the temporary stoppage or absorption of all urethral flow, or relaxing the detrusor muscles to minimize unwanted contractions. The disadvantages and limitations of the prior art treatments are numerous and include:

an excessively high level of patient interaction is typically required to operate and/or maintain the devices, especially for elderly patients and for physically or mentally challenged patients;

limited clinical efficacy;

restricted urine outflow;

patient discomfort and side effects;

urethral and bladder infections related to the devices used; and relatively expensive when compared to non-clinical solutions (diapers, pads, etc.).

These prior art approaches do not address the reduction in dynamic compliance which results in increased intravesical bladder pressure.

SUMMARY OF THE INVENTION

Embodiments of the present invention generally provide methods and devices for use within the body to measure and/or attenuate and/or manage pressure waves in incompressible fluids in organs and tissues of the body. Embodiment of pressure accumulators include either single units or multiple units of single or multichambered devices, diaphragmatic structures, bellows of various forms, and active and passive mechanical structures capable of managing energy, and instrumentation for the clinical use of the devices.

Particular embodiments of the present invention overcome the limitations of the above-described methods and devices for treating urinary tract disorders by increasing the effective dynamic compliance of the bladder or other anatomical structure or system by adding a compliant member to a semi- or non-compliant system. Methods and apparatus of embodiments of the present invention eliminate or reduce the symptoms of patients suffering from one or more of the symptoms of incontinence, overactive bladder, neurogenic bladder, frequency, urgency, interstitial cystitis, and other disorders of the urinary tract by reducing transient pressure changes including impulsive pressure spikes in the urinary tract due to a number of common actions such as coughing, jumping, laughing or sneezing. In addition, apparatus and methods of embodiments of the present invention minimize the possibility of patient suffering caused by patient retention, irritation or infection concerns. In addition, the apparatus and methods of the embodiments of the present invention can address multiple symptoms suffered by the same patient. In addition, devices and methods of embodiments of the present invention are simple and do not necessarily require cystoscopy to place and/or remove the devices.

There is provided in accordance with one aspect of the present invention, a method of attenuating pressure and/or deflecting pressure waves in an anatomical structure. The method comprises the steps of placing an attenuator in communication with a body cavity, and exposing the attenuator to a change in pressure within the cavity. The change in pressure is thereafter attenuated. Generally, the change in pressure is an increase in pressure. In one embodiment, the placing a step comprises placing the attenuator within the cavity. In one application of the invention, the cavity is within the bladder.

Preferably, attenuating the increased pressure is accomplished by a reduction in volume of the attenuator. The reduction in volume is preferably responsive to the increase in pressure. In one embodiment, the attenuator comprises a compressible wall which compresses in response to intravesical pressure to reduce the volume of the attenuator thereby attenuating intravesical pressure spikes.

In accordance with another aspect of the present invention, there is provided a method of treating stress or urgency incontinence, or other urinary tract dysfunction. The method comprises the steps of identifying a patient exhibiting symptoms of a urinary tract dysfunction, and positioning a compressible pressure attenuator in the patient's bladder. The positioning step preferably comprises carrying the attenuator transurethrally into the bladder on a deployment device. The method may further comprise the step of removing the attenuator from the bladder. Preferably, the compressible pressure attenuator maintains the intravesical pressure below the urethral leak point pressure, which is generally within the range of from about 80 cm $H_2O$ or less to about 120 cm $H_2O$.

In accordance with another aspect of the present invention, there is provided a device for treating urinary tract dysfunction. The device comprises a compressible attenuator having an expanded volume within the range of from about 10 cc to about 50 cc, which is compressible to no more than about 80% of its expanded volume under a pressure of about 80 cm $H_2O$ (range 80 cm $H_2O$ to 120 cm $H_2O$). In one embodiment, the attenuator comprises an inflatable balloon. In an alternate embodiment, the attenuator comprises a compressible bellow. In either embodiment, the attenuator may further comprise a pressure transducer, and an inflation port. Embodiments provided with an inflation port are preferably additionally provided with a valve, for inflating the attenuator within the bladder.

In accordance with a further aspect of the present invention, there is provided a method of treating a patient. The method comprises the steps of providing a compressible attenuator which is movable from a first, introduction configuration to a second, implanted configuration. The attenuator is introduced into the body while in a first configuration, and it is transformed within the body to the second configuration. The attenuator thereafter attenuates a pressure spike within the body by reversibly reducing the volume of the attenuator in response to the pressure spike.

In one application, the introducing step comprises transurethrally introducing the attenuator into the bladder. The transforming step comprises at least partially inflating the attenuator. Alternatively, the transforming step comprises permitting the attenuator to transform under its own bias. Preferably, the attenuating step comprises reducing the volume of the attenuator by at least about 5%, preferably at least about 10%, and, if necessary to attenuate a pressure spike, by at least about 25%. The method may further comprise the step of removing the attenuator from the body.

In accordance with yet a further aspect of the present invention, there is provided a method of estimating the dynamic compliance of the bladder. The method comprises the steps of infusing a volume of liquid into the bladder, and measuring the intravesical pressure in the bladder. The infusing step may comprise infusing a volume of at least about 50 cc's over a time of no more than about 10 seconds. In one application, the infusing step is accomplished through a first lumen of a catheter, and the measuring step is accomplished through a second lumen of the catheter.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 9 is a schematic representation of the deployment device of FIG. 6, transurethrally positioned within the bladder.

FIG. 10 is a schematic illustration as in FIG. 9, with the attenuator inflated.

FIG. 13 is a schematic view of a toroidal shaped attenuator in accordance with one embodiment of the present invention.

FIG. 25A is a cross-sectional schematic view as in FIG. 25, illustrating the compression of the primary attenuator in response to elevated abdominal pressure, and the corresponding expansion of the secondary inflatable component.

FIG. 25B is an enlarged fragmentary schematic view of the inflatable component in FIG. 25A.

FIG. 25C is a pressure curve showing the intravesical pressure compared to the secondary balloon pressure.

DETAILED DESCRIPTION OF PREFERRED EMBODIMENTS

Embodiments of the present invention are directed to methods and apparatus for measuring and/or attenuating and/or baffling transient pressure waves in relatively incompressible materials in organs of the body. Illustrative embodiments of the present invention discussed below relate generally to the fields of urology and gynecology, and in particular to the treatment of disorders of the urinary tract exacerbated by sudden fluctuations in intravesical pressure. However, as will be readily understood by those skilled in the art, and as described below, the present invention is not limited to the fields of urology and gynecology and methods and apparatus of embodiments of the present invention may be used in other organs of the body as well to attenuate and/or baffle pressure transients or reversibly occupy intraorgan space.

Embodiments of the present invention dampen transient intravesical pressure including pressure spikes experienced by the urinary tract. During a high frequency transient pressure event, the bladder becomes a relatively non-compliant environment due to a number of factors including the pelvic skeletal structure, the compressive loads of contracting tissues bounding the bladder or the decreased compliance of the musculature, nerve or connective tissue of the bladder. The factors contributing to the reduced compliance of the bladder are aging, anatomic abnormalities or trauma to the structures of the pelvis and abdomen.

Figure 1:
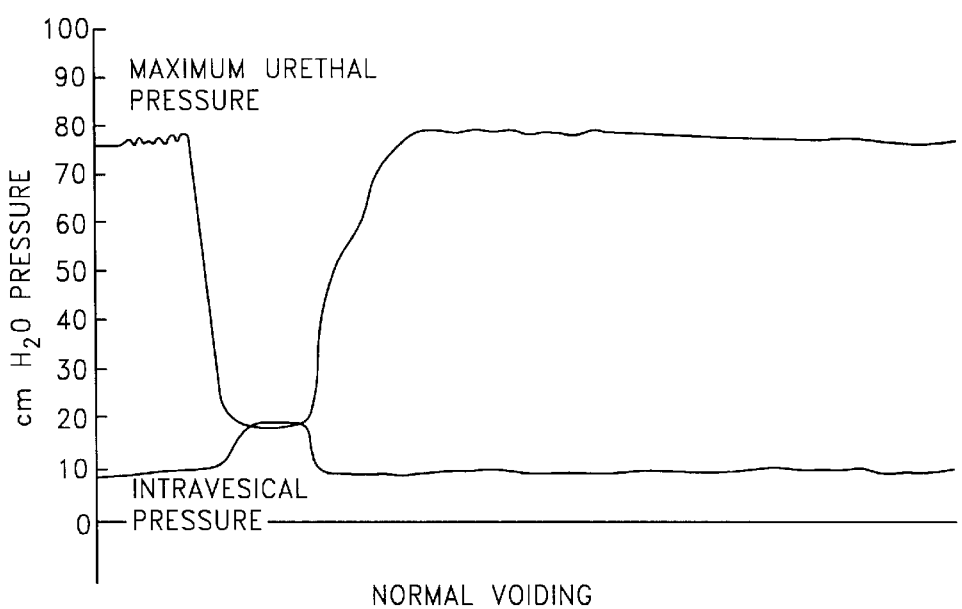
FIG. 1 illustrates maximum urethral pressure against intravesical pressure during normal voiding.

Urine is primarily composed of water and is virtually incompressible in the typical pressure ranges present within the human bladder. The relationship between the maximum urethral pressure and the intravesical pressure for normal voiding of the bladder is well defined. Relaxation of the urethra occurs shortly after the detrusor muscle contracts to cause the intravesical pressure to exceed the urethral pressure. See e.g., FIG. 1.

Figure 2:
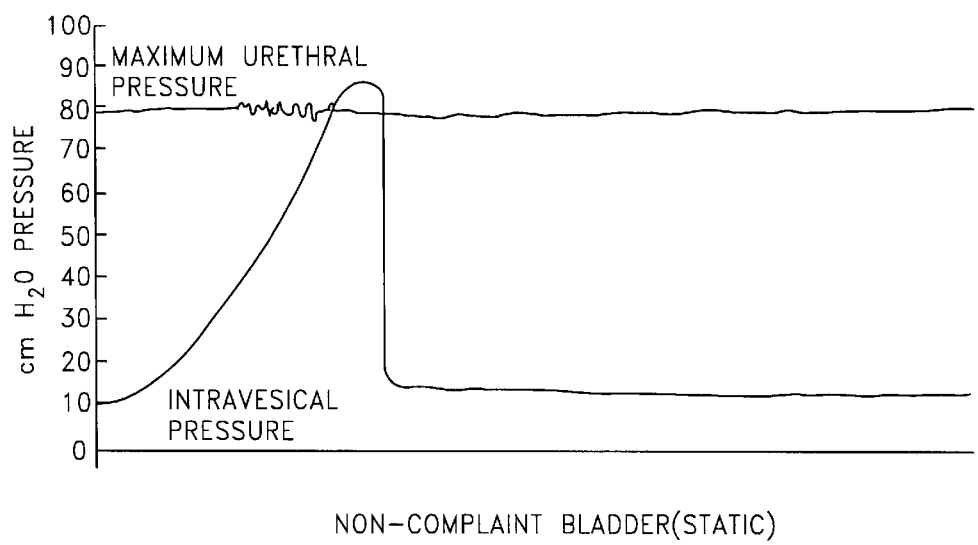
FIG. 2 illustrates the intravesical pressure exceeding the maximum urethral pressure in a noncompliant bladder.

The bladder serves two mechanical functions: 1) low-pressure storage and 2) high-pressure voiding. During the storage or filling phase, the bladder receives an influx of urine from the kidneys. Compliance of the bladder is defined as the ratio of the change in volume to the change in pressure, and the static compliance of the bladder is measured during a typical urodynamic evaluation. The static compliance index in measured by filling the bladder to cystometric capacity and allowing the pressures to equilibrate for a time period of approximately sixty seconds. The static compliance index is calculated by dividing the bladder capacity by the Detrusor pressure at the end of filling. A normal bladder will exhibit static compliance between 21 and 100 ml/cm $H_2O$. A low static compliance bladder typically will have a compliance index of less than 20 ml/cm $H_2O$. A low static compliance bladder typically is poorly distensible and has a high end-filling pressure. See FIG. 2. The steady state compliance of the bladder is used to diagnose patients with naturopathic problems such as damage to the lower motor neurons, upper motor neurons, or multiple sclerosis. In addition, the steady state compliance of the bladder is also used, in some cases, to attempt to diagnose problem of incontinence, including urgency, frequency and cystitis.

In general, intravesical pressure spikes result from volumetric tissue displacement in response to gravity, muscular activity or rapid acceleration. The lack of compliance of the bladder and the urine contained in the bladder with respect to events of high frequency, result in minimal fluidic pressure attenuation of the higher frequency pressure wave(s) and results in high intravesical pressures that are directly transmitted to the bladder neck and urethra, which may or may not cause detrusor contractions. Under these conditions, the urethra may act as a volumetric pressure relief mechanism allowing a proportional volume of fluid to escape the bladder, to lower the intravesical pressure to a tolerable level. The urethra has a maximum urethral pressure value, and when the intravesical pressure exceeds the maximum urethral pressure, fluid will escape the bladder. Under these conditions, nerve receptors in the bladder and/or bladder neck and/or trigone trigger a detrusor contraction that may lead to matriculation (frequency) or may subside without matriculation (urgency) or may lead to the intravesical pressure exceeding the maximum urethral pressure resulting in fluid escaping the bladder (urge incontinence). Under these conditions, waves hitting and/or expanding the bladder wall, may cause a patient with cystitis to exhibit significant pain.

The inventors of the present application have recognized that for the vast majority of patients suffering from problems of urinary tract disorders such as frequency, urgency, incontinence and cystitis, the cause and/or contributor to the bladder dysfunction is a reduction of overall dynamic bladder compliance rather than steady state bladder compliance. These patients may often have bladders that are compliant in steady state conditions, but have become non dynamically compliant when subjected to external pressure events having a short duration of, for example, less than 5 seconds or in some cases less than 2 seconds or even less than 0.5 seconds. Reduction in dynamic compliance of the bladder is often caused by some of the same conditions as reduction of steady state compliance including aging, use, distention, childbirth and trauma. The anatomical structure of the bladder in relation to the diaphragm, stomach, and uterus (for women) causes external pressure to be exerted on the bladder during talking, walking, laughing, sitting, moving, turning, and rolling over.

Figure 3:
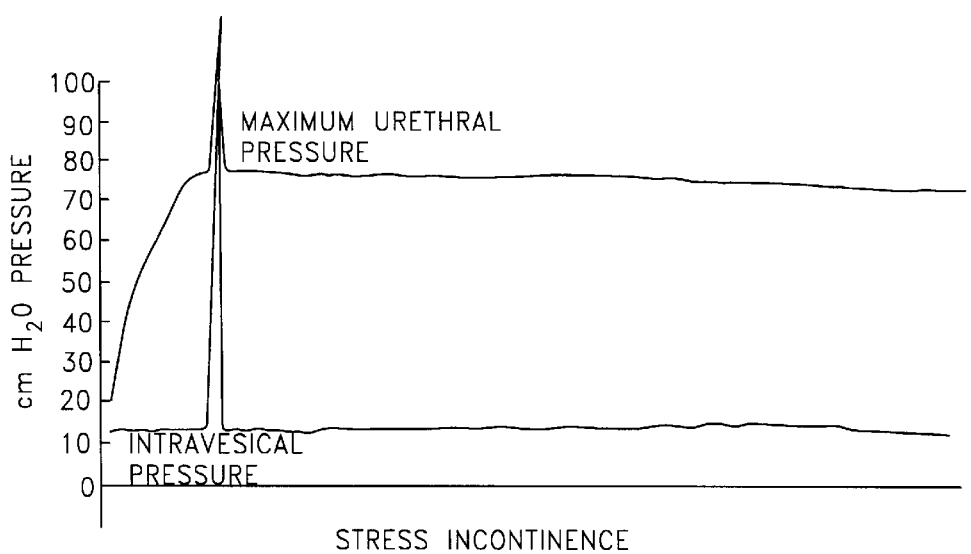
FIG. 3 illustrates an intravesical pressure spike exceeding the maximum urethral pressure during stress incontinence.

The relationship between intravesical pressure and the maximum urethral pressure for a patient suffering from stress incontinence due to lack of dynamic compliance in the bladder is illustrated in FIG. 3. When the patient coughs (or some other stress event occurs), if the bladder does not have sufficient dynamic compliance in that frequency range a spike will occur in the intravesical pressure. Intravesical pressure spikes in excess of 120 cm $H_2O$ have been urodynamically recorded during coughing, jumping, laughing or sneezing. When the intravesical pressure exceeds the maximum urethral pressure value, leakage occurs. In order to retain urine during an intravesical pressure spike, the urinary retention resistance of the continent individual must exceed the pressure spike. Urinary retention resistance can be simplified as the sum total of the outflow resistance contributions of the urethra, bladder neck and meatus. In female patients, it is generally believed that the largest resistance component is provided by the urethra. One measure of urinary resistance is the urodynamic measurement of urethral leak pressure. The incontinent individual typically has a urethral leak pressure less than 80 cm $H_2O$. The decline of adequate urinary retention resistance has been attributed to a number of factors including reduced blood flow in the pelvic area, decreased tissue elasticity, neurological disorders, deterioration of urethral muscle tone and tissue trauma.

Figure 4:
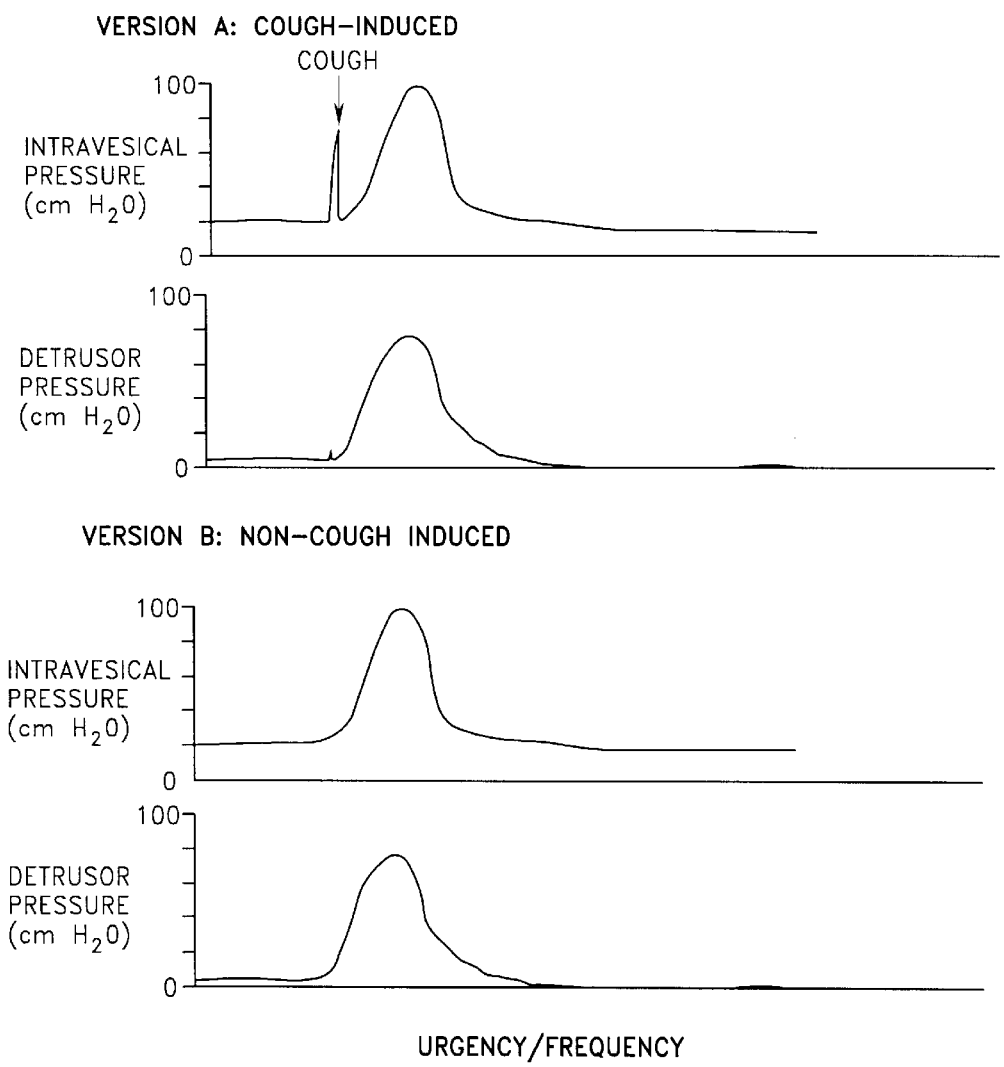
FIG. 4A illustrates the relationship between intravesical pressure and detrusor pressure during cough-induced urgency or frequency.
FIG. 4B illustrates the relationship between intravesical pressure and detrusor pressure during non-cough-induced urgency or frequency.

Urinary disorders, such as urgency, frequency, otherwise known as overactive bladder, and interstitial cystitis are caused or exacerbated when rapid pressure increases or rapid volume increases or other irritable conditions within the bladder cause motor neurons to send signals to the brain to begin the cascade of events necessary for urination. External pressure exerted on the bladder may result in a detrusor contraction they may result in urgency, frequency or incontinence. See FIG. 4. Urinary disorders such as interstitial cystitis or irritable bladder conditions are a chronic inflammatory condition of the bladder wall, which includes symptoms of urgency and/or frequency in addition to pain. Therefore, the problem of a pressure spike in the functionally noncompliant bladder can be further exacerbated by a nearly simultaneous contraction of the bladder and a relaxation of the urethra that occurs as a result of the stimulation of higher cognitive centers. The contraction of the bladder and relaxation of the urethra will typically be slightly delayed in time from the occurrence of the spike, and if unexpected may result in a more significant leakage than that caused by the pressure spike alone.

Embodiments of the present invention provide methods and devices for measuring and reporting the dynamic compliance of the bladder. One method of determining dynamic compliance includes the rapid infusion of a volume of fluid into the bladder with immediate measurement of the intravesical pressure. The volume would be more than 50 ccs, preferably greater than 100 cc and more preferably greater than 200 cc. The rate of infusion would be less than 10 seconds, preferably less than 5 seconds, and more preferably less than 2 seconds. One embodiment of this invention includes a two lumen catheter placed within the bladder, wherein a compliant balloon is rapidly filled with a non-compliant material, such as saline is infused through one lumen of the catheter. The resulting intravesical pressure is measured from the other lumen of the catheter. This infusion can be with a syringe, a mechanically assisted syringe or pump.

An additional embodiment provides methods and devices for treating and/or compensating for reduced dynamic compliance of the bladder. In other embodiments of the present invention, a device having a compressible element is placed within the human urinary bladder, in a manner that allows the compressible element to act as a pressure accumulator to attenuate transient pressure events. Gases such as atmospheric air, carbon dioxide and nitrogen are very compressible in the pressure ranges typically encountered in the human bladder, and these gases may be used in air cell-type devices inserted in the bladder. Furthermore, when compared to the tissues encompassing urine, these gases are significantly more compliant than the immediate environment. The addition of a proportionately smaller volume of unpressurized gas acts as a low rate spring in series with the native fluidic circuit of the urinary tract.

In other embodiments of the present invention, the compression of the enclosed volume of air creates heat that is dissipated into the relatively infinite heat sink of the body. The balance of the energy absorbed by the compressed air is simply returned at a different, lower frequency into the fluidic circuit when the gas is allowed to expand, as the surrounding tissues return to their initial positions. The addition of adequate local compliance can effectively attenuate transient intravesical pressure spikes to levels below the patient's leak pressure, thus obviating the need for relief by means of volumetric displacement of urine, and/or preventing the stimulation of signals to the brain that cause bladder contractions.

One pressure compensation device of the present invention that is placed within the human urinary bladder will now be described. The device is intended to be unteathered in the bladder and is intended to remain in the bladder for between several hours and one year, between one week and six months, or between one and three months. The device is a small elastomeric air cell with a relaxed (unstretched) volume of between 1 and 500 cc, more preferably between 1 and 100 cc and more preferably still, between 3 and 25 cc. The device is a unitary component but can be comprised of two or more subcomponents. The device has a substantially uniform wall thickness of between 0.25 inch to 0.0001 inch, more preferably between 0.0005 inch and 0.005 inch, but could be designed to vary greatly, and still perform the intended function. In the embodiment described above, devices having air cells that are free-floating in the bladder have been described. In other embodiments of the present invention, air cells or similar devices could be surgically affixed to the bladder wall through the use of suture, staples and other accepted methods. Other embodiments could also include devices with programmable, variable and adjustable buoyancy by using ballasting, specific inflation/deflation solutions, alternative materials of construction or by other means.

Figure 5:
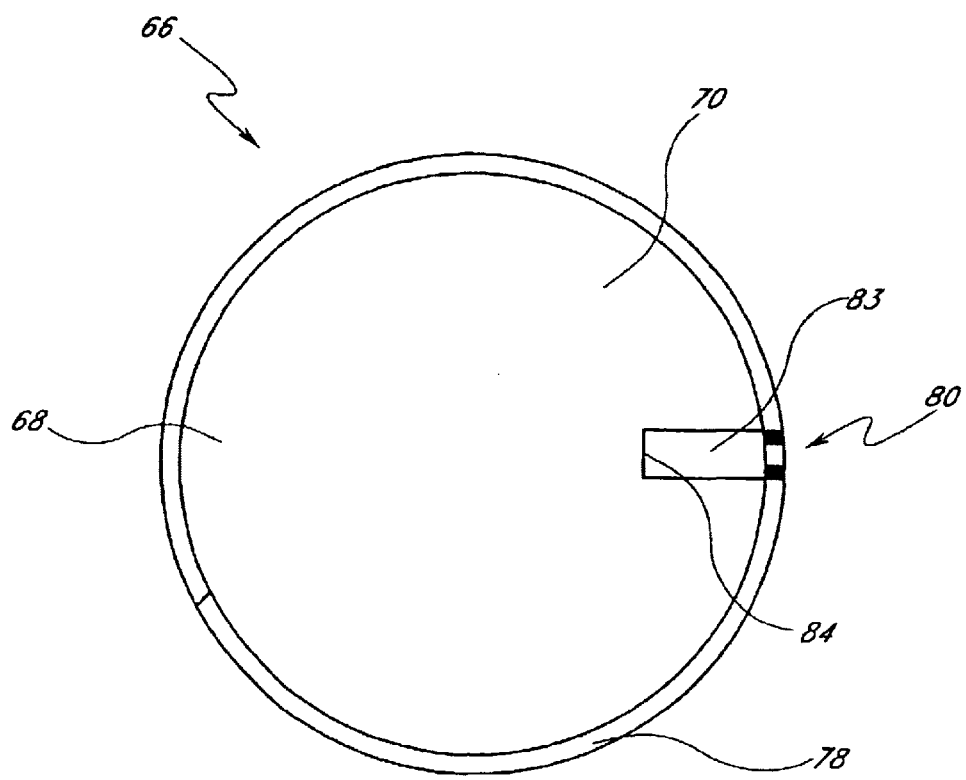
FIG. 5 is a schematic top plan view of an inflatable attenuator in accordance with one aspect of the invention.
Figure 5A:
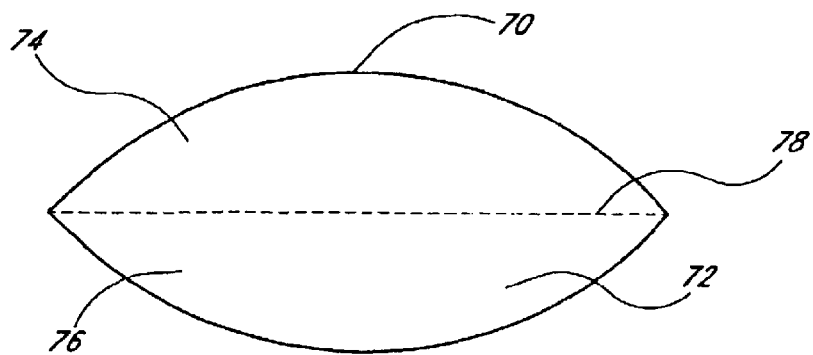
FIG. 5A is a side elevational cross-section through the attenuator of FIG. 5.

Referring to FIG. 5, there is illustrated one embodiment of an attenuator 66 which comprises a moveable wall such as on an inflatable container 68. The inflatable container 68 is illustrated as having a generally circular profile, although other profiles may be utilized in accordance with the present invention. The diameter of the inflatable container 68 may be varied within the range of from about 1 inch to about 6 inches, in an application of the invention involving the implantation of only a single attenuator. Many embodiments of the inflatable containers 68 will have a diameter within the range from about 1 inch to about 3 inches, with a total volume within the ranges recited above. In general, the specific dimensions and configuration of the container 68 are selected to produce an attenuator having a desired volume and a desired dynamic compression range, and may be varied from spherical to relatively flat as will be apparent to those of skill in the art based upon the disclosure herein.

In certain embodiments, two or three or more discreet inflatable containers 68 are utilized. The sum of the volumes of the multiple containers will equal the desired uncompressed displacement.

The inflatable container 68 illustrated in FIG. 5 comprises a flexible wall 70, for separating the compressible contents of the attenuator 66 from the external environment. Flexible wall 70 comprises a first component 74 and second component 76 bonded together such as by a seam 78. In the illustrated embodiment, the first component 74 and second component 76 are essentially identical, such that the seam 78 is formed on the outer periphery of the inflatable container 68. Seam 78 may be accomplished in any of a variety of manners known in the medical device bonding arts, such as heat bonding, adhesive bonding, solvent bonding, RF or laser welding, or others known in the art.

The flexible wall 70 formed by a bonded first component 74 and second component 76 define an interior cavity 72. As is discussed elsewhere herein, interior cavity 72 preferably comprises a compressible media, such as gas, or foam. Alternatively, media or structures capable of reduction in volume through a mechanism other than strict compression may also be used. For example, a material capable of undergoing a phase change from a first, higher volume phase to a second, lower volume phase under the temperature and pressure ranges experienced in the bladder may also be used.

In order to minimize trauma during delivery of the attenuator 66, the attenuator is preferably expandable from a first, reduced cross-sectional configuration to a second, enlarged cross-sectional configuration. The attenuator 66 may thus be transurethrally deployed into the bladder in its first configuration, and enlarged to its second configuration once positioned within the bladder to accomplish the pressure attenuation function. Preferably, a crossing profile or a greatest cross-sectional configuration of the attenuator 66 when in the first configuration is no greater than about 24 French (8 mm), and, preferably, no greater than about 18 French (6 mm). This may be accomplished, for example, by rolling a deflated inflatable container 68 about a longitudinal axis, while the interior cavity 72 is evacuated.

Once positioned within the bladder, the interior cavity 72 is filled with the compressible media to produce a functional attenuator 66. The present inventors contemplate fill pressures of generally less than about 1.5 atmospheres, and, in some embodiments, less than one atmosphere in the case of an air filled collapsible attenuator 66. In general, the fill pressure is preferably no more than necessary to keep the attenuator 66 fully inflated in the absence of pressure spikes. Excessive pressure within the attenuator 66 may shorten the dynamic range of the attenuator 66, thereby lessening the sensitivity to attenuate pressure spikes. Pressures of less than 1 atmosphere, or even vacuums may be utilized if the structure of the attenuator is sufficient to balance the negative pressure to produce a net force such that attenuation can occur. This may be accomplished, for example, in an embodiment where the attenuator 66 is provided with a self expandable support structure (e.g. nitinol wire frame) which provides a radially outwardly directed bias.

The resiliency of the material of the attenuator, and the pressure of the inflation media are preferably also matched to produce a compression cycle time which is fast enough to allow the attenuator to respond to increases in pressure that the device does not have a clinically detrimental effect on voiding. For example, the attenuator compression cycle preferably bottoms out or reaches a maximum in a sufficiently short period of time as detrussor pressure increases that adverse clinical effects on voiding are minimized or prevented.

To facilitate filling the interior cavity 72 following placement of the attenuator 66 within the bladder, the inflatable container 68 is preferably provided with a valve 80. In the illustrated embodiment, valve 80 is positioned across the seam 78, and may be held in place by the same bonding techniques utilized to form the seam 78. Valve 80 may be omitted in an embodiment in which the attenuator 66 is self-expandable.

Valve 80 generally comprises an aperture 82, for receiving a filling tube therethrough. Aperture 82 is in fluid communication with the interior cavity 72 by way of a flow path 83. At least one closure member 84 is provided for permitting one way flow through flow path 83. In this manner, a deployment and filling device can be utilized to displace closure member 84 and introduce compressible media into the interior cavity 72. Upon removal of the filling device, the closure member 84 prevents or inhibits the escape of compressible media from the interior cavity 72 through the flow path 83.

Thus, the closure member 84 is preferably movable between a first orientation in which it obstructs effluent flow through the flow path 83 and a second position in which it permits influent flow through the flow path 83. Preferably, the closure member 84 is biased in the first direction. Thus, forward flow may be accomplished by either mechanically moving the closure member 84 into the second position such as using a filling tube, or by moving the closure member 84 into the second position by exerting a sufficient pressure on the compressible media in flow path 83 to overcome the closure bias. Certain specific valve structures will be described in connection with FIGS. 8A–E below. However, any of a wide variety of valve designs may be utilized in the attenuator 66 of the present invention as will be apparent to those of skill in the art in view of the disclosure herein.

In one embodiment of the present invention, the device consists of an air cell consisting of 0.0018 inch thick polyurethane sheets that have been bonded together to form a 2⅜ inch circle in top view. In one embodiment, the device is made from polyurethane and is intended to be inflated to a pressure of about 1 atm or generally within the range of 0.5 to 1.5 atm. Integral to the sealing edge 78 of the device holds a port/valve 80 utilized in the placement, inflation and release of the device. Into the port/valve structure 80 is placed the distal end of a rigid fill tube (0.050 OD) 50. The valve 80 employed may be one of the valves described in U.S. Pat. No. 5,144,708, which is incorporated herein by reference. In an alternate embodiment, the device may be sealed in situ following inflation, in which case the valve may be omitted.

Biocompatible lubricating substances may be used to facilitate the placement of the device/fill tube within the lumen of the introducer. The distal tip of the introducer has been modified to allow a minimally traumatic presentation of the device to the urethral tissue. Biocompatible lubricating substances may be used to facilitate the insertion of the device into the urethra.

Figure 6:
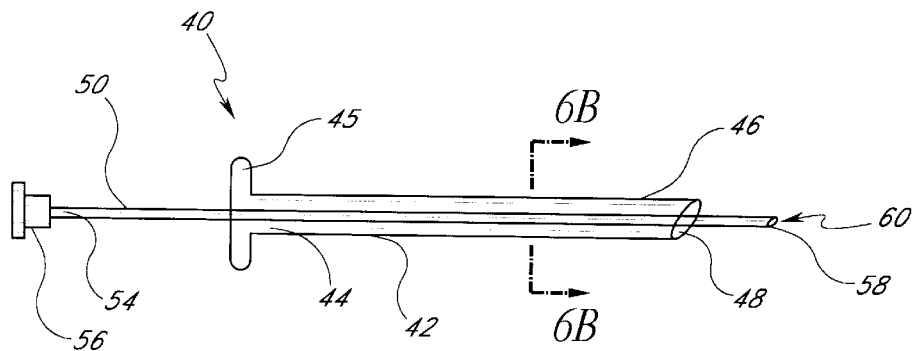
FIG. 6 is a side elevational schematic view of an attenuator deployment device in accordance with one aspect of the present invention.

Referring to FIG. 6, there is illustrated one attenuator deployment device in accordance with the present invention. In general, the deployment device 40 is designed to advance an attenuator 66 (not illustrated) transurethrally into the bladder while in a first, reduced cross-sectional configuration, and to thereafter inflate or enlarge or permit the expansion of the attenuator to a second, implanted orientation. The particular configuration and functionality of the deployment device 40 will therefore be governed in large part by the particular design of the attenuator 66. Thus, as will be apparent to those of skill in the art in view of the disclosure herein, various modifications and adaptations may become desirable to the particular deployment device disclosed herein, depending upon the construction of the corresponding attenuator.

The deployment device 40 comprises an elongate tubular body 42 having a proximal end 44 and a distal end 46. Tubular body 42 is dimensioned to transurethrally access the bladder. Thus, the tubular body 42 preferably has an outside diameter of no more than about 8 mm, and, preferably, no more than about 6 mm. The length of the tubular body 42 may be varied, depending upon the desired proximal extension of the deployment device 42 from the urethra during deployment. In general, an axial length of tubular body 42 within the range of from about 2" to about 10" for adult female patients and from about 4" to about 20" for adult male patients is currently contemplated.

The tubular body 42 is provided with at least one central lumen 48 extending axially therethrough. Central lumen 48 axially slideably receives a filling tube 50, for filling the attenuator 66. Filling tube 50 comprises a tubular body 52 having a proximal end 54 and a distal end 58. An inflation lumen 60 extends throughout the length of the tubular body 52, and is in fluid communication with a proximal hub 56. Hub 56 comprises a connector such as a standard luer connector for coupling to a source of inflation media.

The tubular body 52 has an axial length which is sufficiently longer than the axial length of tubular body 42 to allow the proximal hub 56 to remain accessible to the clinician and accomplish the functions of deploying and filling the attenuator 66. In one embodiment, an outer tubular sheath (not illustrated) is slideably carried over the tubular body 42, and is spaced radially apart from the tubular body 52 to define an annular cavity for receiving a rolled attenuator 66 therein. In this manner, the deflated attenuator can be rolled around a distal portion of the tubular body 52 and carried within the tubular sheath during transurethral placement. Once the deployment device 40 has been properly positioned, proximal retraction of the outer sheath with respect to the tubular body 52 exposes the deflated attenuator 66. A source of inflation media is coupled to the proximal hub 56, and media is introduced distally through central lumen 60 to inflate the attenuator 66. Following inflation of the attenuator 66, the deployment device 40 is disengaged from the attenuator 66, such as by retracting the filling tube 50 with respect to the tubular body 42. A distal stop surface 47 on tubular body 42 prevents proximal movement of the attenuator 66 as the filling tube 50 is proximally retracted. Deployment device 40 is thereafter removed from the patient, leaving the inflated attenuator 66 within the bladder.

Figure 6A:
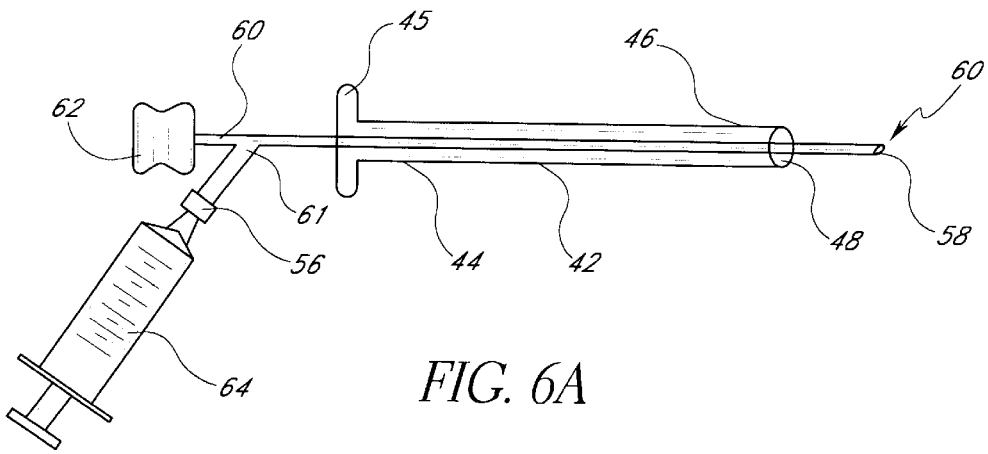
FIG. 6A is a side elevational schematic view of an alternate embodiment of the present invention.
Figure 6B:
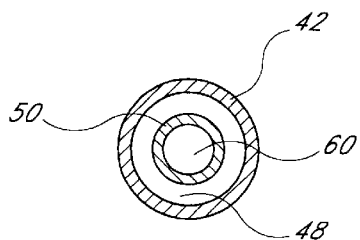
FIG. 6B is a cross-section through the line 6B—6B in FIG. 6.

Referring to FIG. 6a, there is illustrated a modified version of the deployment device 40. In this embodiment, a control 62 is connected by way of a proximal extension 60 to the tubular body 52. The control 62 may be in any of a variety of forms, such as a knob or a pistol grip. The control 62 may be grasped by the clinician, and utilized to axially advance or retract the filling tube 50 within the tubular body 42. The proximal hub 56 is connected to the tubular body 52 by way of a bifurcation 61. As will be appreciated by those of skill in the art, the central lumen 60 extends through the bifurcation 61 and to the proximal hub 56. Proximal extension 60 may comprise a blocked tubular element or a solid element. An inflation source 64 such as a syringe filled with a predetermined volume of air or other media may be connected to the proximal hub 56.

For patient comfort, the introducer is suitably sized to easily pass through the urethra (approximately 0.5 to 4 mm diameter). Visual feedback is provided to the clinician by means of insertion depth indicators along the longitudinal length of the introducer. The introducer may also have an adjustable depth stop that allows the clinician to pre-set the desired insertion depth. Once the device has been inserted into the urethra to the desired depth the introducer is then kept in a fixed position and the device mounted on the distal end of the fill tube is then extended in the lumen of the bladder. The device is then filled with the indicated volume of gas from the attached syringe or similar device. Once properly inflated, the device is released from the fill tube using the tip of the introducer as an opposing force disengaging the device valve from the fill tube. The fill tube is then retracted completely into the lumen of the introducer and the entire assembly is then withdrawn from the patient. The device is left in place for the clinically indicated period of time.

Figure 7A:
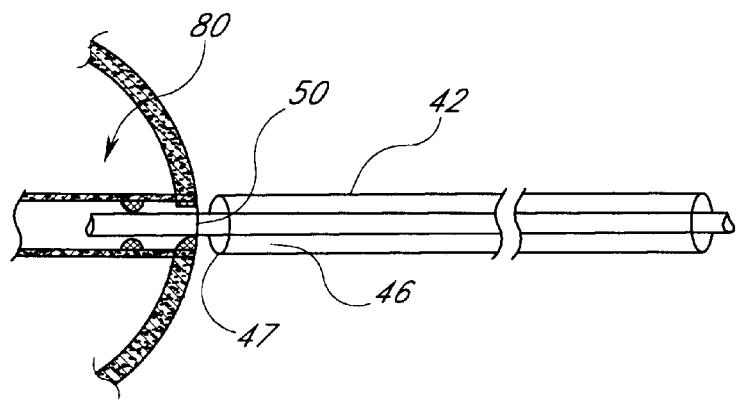
FIG. 7A is a fragmentary schematic view of the filling tube of a deployment device engaged within the valve of an attenuator.
Figure 7B:
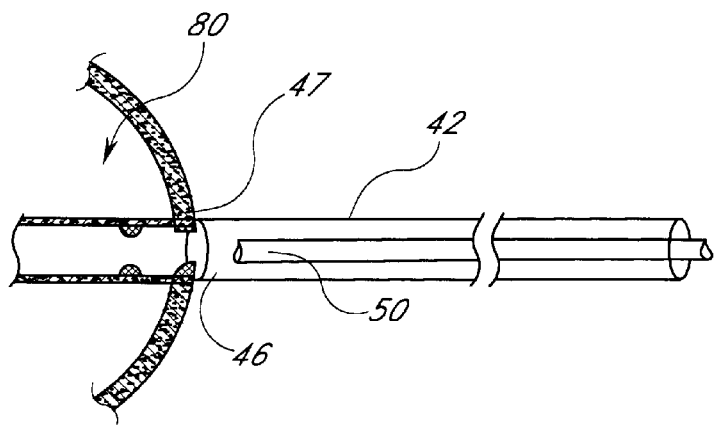
FIG. 7B is a fragmentary schematic view as in FIG. 7A, with the filling tube proximally retracted from the valve.
Figure 7C:
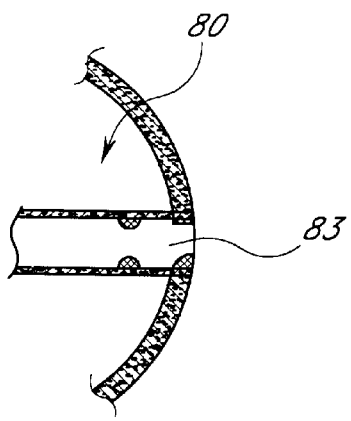
FIG. 7C is a fragmentary schematic view as in FIG. 7B, with the deployment device removed from the attenuator.

Referring to FIGS. 7A–C, there is illustrated one disengagement sequence for deploying the inflatable attenuator 66 from the deployment device 40 in accordance with one aspect of the present invention. As illustrated in FIG. 7a, the deployment device 40 is initially configured with the filling tube 50 positioned within the valve 80. The distal end 46 of outer tubular body 42 is dimensioned such that it will not fit through the aperture 82 of valve 80. Once the attenuator 66 has been positioned within the bladder, the attenuator 66 is inflated through filling tube 50.

Referring to FIG. 7B, the filling tube 50 is proximally retracted following inflation so that it disengages from the valve 80. This is accomplished by obstructing proximal movement of the attenuator 66 by stop surface 47 on the distal end 46 of tubular body 42. The attenuator 66 is thereafter fully disengaged from the deployment device 40, and the deployment device 40 may be removed.

Figure 8A:
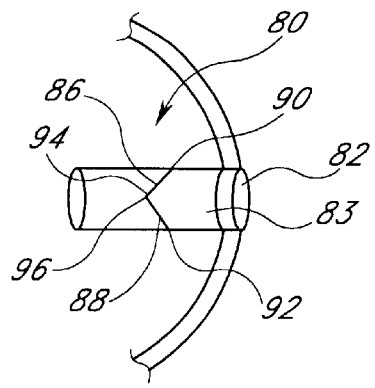
FIGS. 8A—8E schematically illustrate different valve constructions for an inflatable attenuator in accordance with the present invention.

Referring to FIG. 8A, there is illustrated a duck bill embodiment of the valve 80. Valve 80 comprises a tubular wall 81, having an aperture 82 in communication with a flow path 83. At least one closure member 84 is attached to the tubular wall, and extends across the flow path 83. In the illustrated embodiment, closure member 84 comprises a first and a second duck bill valve leaflets 86 and 88 which are attached at lateral edges 90 and 92 to the tubular wall. The leaflets 86 and 88 incline medially in the distal direction to a pair of coaptive edges 94 and 96. This configuration allows forward flow through flow path 83 to separate coaptive edges 94 and 96, thereby enabling inflation of the attenuator 66. Upon removal of the inflation media source, the inflation media within attenuator 66 in combination with natural bias of the leaflets 86 and 88 cause the leaflets to coapt, thereby preventing effluent flow of inflation media through the flow path 83.

The tubular body 81 and first and second leaflets 86 and 88 may be manufactured from any of a variety of materials which will be apparent to those of skill in the art. For example, tubular body 81 may be made from polyurethane such as by extrusion. Leaflets 86 and 88 may be made from any of a variety of flexible materials such as polyurethane, silicone, or polyethylene, and may be bonded to the tubular element 81 using adhesives, heat bonding, or other bonding techniques known in the art. Suitable valves include the valve manufactured by Target Therapeutics and sold as the DSB silicon balloon to fill aneurysms and arterial-venous malformations.

Figure 8B:
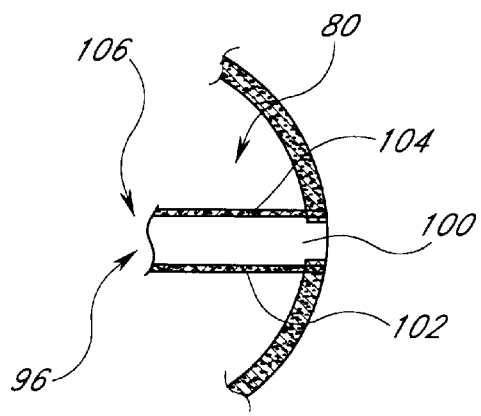

Referring to FIG. 8B, closure is accomplished by two coaptive edges on distal end 106 of tubular body 81. This construction is sometimes referred to as a flapper valve. The tubular body 81 in this embodiment is formed by a first wall 96 and a second wall 100 which are bonded or folded along a first edge 102 and a second edge 104 to define a flow path 83 extending therethrough. The free distal ends of first and second walls 96 and 100 at the distal end 106 form coaptive leaflets, which may be opened under forward flow pressure through the flow path 83 and will inhibit or prevent reverse flow through the flow path 83.

Figure 8C:
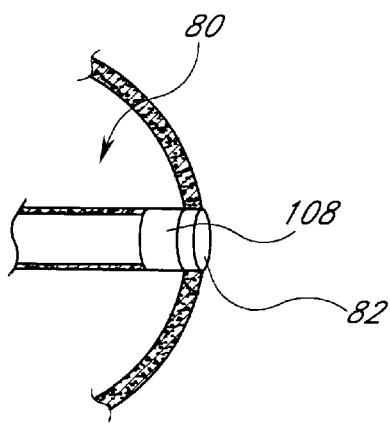

Referring to FIG. 8C, the proximal end of the flow path 83 on the flapper valve of FIG. 8B or other valve structure may be reinforced such as by a reinforcing tube 108. Reinforcing tube 108 may be manufactured in any of a variety of ways. For example, reinforcing tube 108 may be extruded from various densities of polyethylene, PEBAX, polyurethane, or other materials known in the art. Reinforcing tube 108 may be desired to maintain patency of the pathway to the valve 80, particularly in an embodiment adapted for coupling to a deflation and removal device as will be discussed. Alternatively, the reinforcing tube 108 may be removable and used to prevent sealing of the valve during the manufacturing process and may also ease the placement of a fill tube in the valve. This reinforcing tube 108 is removed after the manufacturing process is complete, or may be removed before, during, or after the fill tube is placed.

Figure 8D:
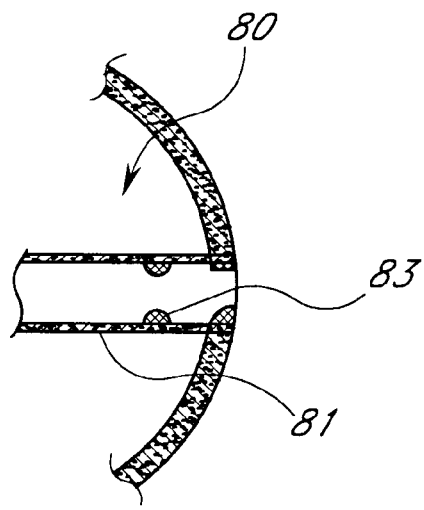

Referring to FIG. 8D, there is illustrated an additional feature which may additionally be incorporated into any of the valves discussed above. In this embodiment, an annular sealing ring 108 is provided on the interior surface of the tubular body 81. Annular sealing ring 108 is adapted to provide a seal with the filling tube 50, to optimize the filling performance of the device. Sealing ring 108 is thus preferably formed from a resilient material such as silicone or polyurethane and dimensioned to slideably receive the filling tube 50 therethrough. Alternatively, sealing with the fill tube may be enhanced by restricting the aperture diameter without the use of a distinct sealing ring 108.

Figure 8E:
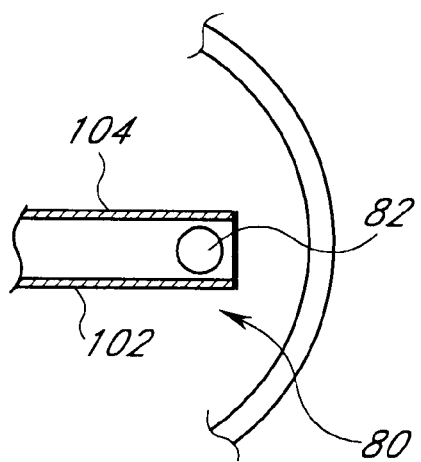
Figures 11, 11A:
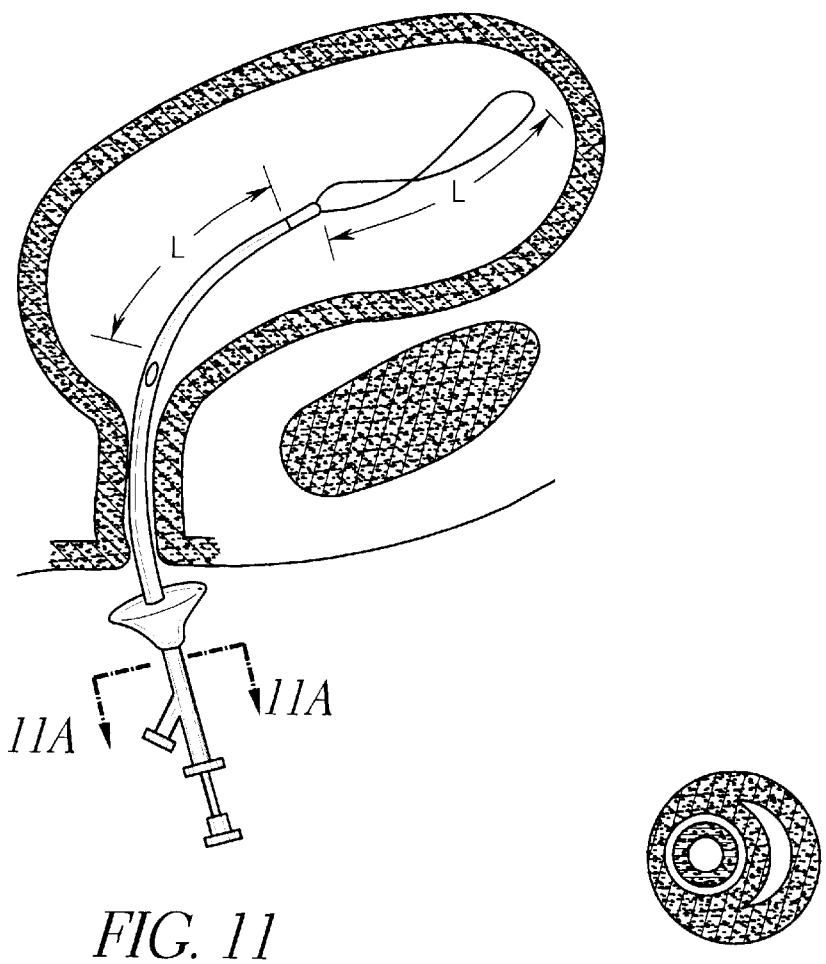
FIG. 11 is a schematic view of an alternate embodiment of a deployment device in accordance with the present invention, transurethrally positioned within the bladder.
FIG. 11a is a cross-section through one embodiment of the deployment device of FIG. 11.

Referring to FIG. 8E, the valve may also be placed in the body of the attenuator, rather in the seam. The valve can be placed in any number of ways including the methods described in U.S. Pat. No. 5,248,275, and U.S. Pat. No. 5,830,780.

The implanted attenuator 66 is preferably also removable from the bladder. Removal may be accomplished in any of a variety of ways, depending upon the construction of the attenuator. Preferably, removal is accomplished transurethrally.

In most embodiments, removal is accomplished by reducing the attenuator 66 from its second enlarged profile to its first, reduced profile so that it may be withdrawn transurethrally by a retrieval device. The retrieval catheter will be configured differently depending upon whether reduction from the second profile to the first profile is accomplished by deflation, or by compression. One embodiment of a retrieval device utilized to remove an inflatable attenuator 66 will be described below in connection with FIG. 12.

An alternative removal procedure involves dissolving or degrading the material or a portion of the material of the attenuator 66 in situ. Material selection and wall thickness of the attenuator 66 may be optimized to provide the desired useful life of the attenuator 66, followed by dissolution in the aqueous environment of the bladder. Alternatively, dissolution or deflation may be catalyzed or accelerated by an accelerating event such as a change in pH or introduction of an initiator or accelerator into the bladder, or reduction of pressure.

Attenuators having a predetermined dwell time after which they are automatically voided advantageously eliminate the need for a removal procedure. Such temporary attenuators can be manufactured in a variety of ways in accordance with the present invention, such as through the use of bioabsorbable materials. In one embodiment, the entire wall of the inflatable container 68 is made from an absorbable material. As used herein "absorbable" means any material which will dissolve, degrade, absorb or otherwise dissipate, regardless of the chemical mechanism, to achieve the purpose recited herein. Alternatively, only a portion of the flexible wall 70 or other portion of the device such as the valve is made from an absorbable material. As soon as one or more windows or "fuse" components of the device is absorbed, the device will deflate through the resulting opening and can be expelled during normal voiding. In a further alternative, one or more seams such as seam 78 can be bonded by a dissolvable or absorbable material that is designed to fail after a predetermined time in the aqueous environment of the bladder. The resulting deflated components from any of the foregoing time limited embodiments can thereafter either be expelled during normal voiding, or can remain in the bladder in a deflated state until removed using a removal device.

The predetermined dwell time within the bladder can be influenced by a variety of design factors, including the formulation of the absorbable material and the physical shape, thickness and surface area of the absorbable component. A variety of absorbable polymers which can be used in the present invention are known in the absorbable suture arts. For example, absorbable multifilament sutures such as DEXON sutures (made from glycolide homopolymer and commercially available from Davis & Geck, Danbury, Conn.), VICRYL sutures (made from a copolymer of glycolide and lactide and commercially available from Ethicon, Inc., Sommerville, N.J., and POLYSORB sutures (also made from a copolymer of glycolide and lactide and commercially available from U.S. Surgical Corporation, Norwalk, Conn.) exemplify materials known in the industry and characterized as short term absorbable sutures. The classification short term absorbable sutures generally refers to surgical sutures which retain at least about 20 percent of their original strength at three weeks after implantation, with the suture mass being essentially absorbed in the body within about 60 to 90 days post implantation.

Certain bioabsorbable elastomers may also be used to form the devices or fuses in accordance with the present invention. The elastomers can be melt-processed, for example by extrusion to prepare sheets, plugs or tubular structures. Alternatively, the copolymers can be injection molded to fabricate intricately designed parts, or compression molded to prepare films. For the details of such melt-processing techniques, see, for example, F. Rodriguez "Principles of Polymer Systems" McGraw Hill, 1970, Chapter 12.

The bioabsorbable elastomers can also be solvent cast to prepare thin films. Solvent casting can be accomplished using conventional methods such as first dissolving the copolymer in a suitable solvent to make a solution, then casting the solution on a glass plate to make a film, and then evaporating the solvent from the cast film. In another processing scheme, the copolymers can be lyophilized to prepare foams. Lyophilization can be accomplished by first dissolving the copolymer in an appropriate solvent, freezing the solution, and then removing the solvent under vacuum. The set of appropriate solvents include p-dioxane. Lyophilization techniques to prepare films are described in Aspects Theoriques Et Industriels De La Lyophilization by Louis Rey, 1964.

Certain bioabsorbable elastomers are disclosed in U.S. Pat. No. 6,113,624 to Bezwada, et al., entitled Absorbable Elastomeric Polymer, the disclosure of which is incorporated in its entirety herein by reference. In accordance with the process disclosed therein, a two-step, one-reaction vessel, two-temperature process is utilized in which a mixture of p-dioxanone monomer and p-dioxanone homopolymer, is formed at low temperatures of from about 100° C. to about 130° C., preferably 110° C. The mixture is then reacted with lactide at temperatures from about 120° C. to about 190° C. to form copolymers in which segments or sequences are composed of both p-dioxanone and lactide repeating units. These segmented copolymers are stated to be less crystalline than the block or graft copolymers previously known in the art and, therefore, yield materials with good strength, but shorter BSR (Breaking Strength Retention) profiles, faster absorption rates, much longer elongations and lower stiffness than the block copolymers. A wide variety of copolymers of polylactic and polyglycolic acids are also known in the art, particularly for use with absorbable orthopedic screws and fasteners.

The ideal material can be optimized through routine experimentation taking into account the attenuator design and the desired indwelling time period. Attenuators may be time rated, such as 15 days, 30 days, 45 days, 90 days, 180 days or other as may be desired. The deflated and or partially dissolved attenuator will be transurethrally expelled within a few days of the expiration of the rated time period from the time of implantation.

Figure 12:
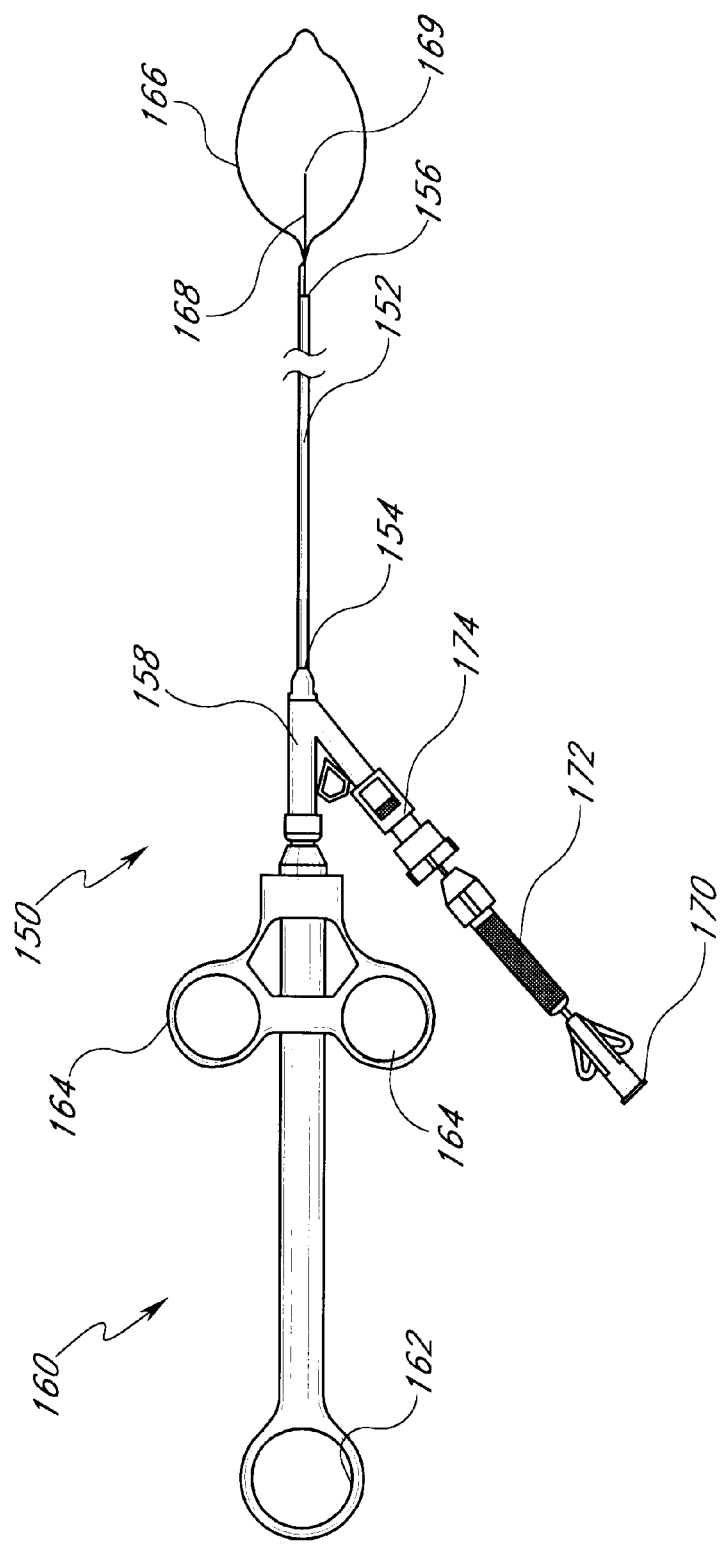
FIG. 12 is a side elevational schematic view of an attenuator removal device in accordance with one aspect of the present invention.

Referring to FIG. 12, there is illustrated a side elevational schematic view of one embodiment of an intravesical removal device in accordance with the present invention. This device is adapted to retrieve the inflatable balloon-type attenuators discussed elsewhere herein. The removal device 150 comprises an elongate tubular body 152 which extends between a proximal end 154 and a distal end 156. Tubular body 152 is dimensioned to transurethrally access the bladder. In one embodiment, the removal device 150 is adapted for use in conjunction with a standard urological cystoscope (e.g., 21–24 French), having a minimum working channel of approximately 3.0 mm. For this purpose, removal device 150 in one embodiment has an overall length of approximately 76 cm and a useable length of approximately 60 cm.

Tubular body 152 may be manufactured in accordance with any of a variety of techniques well understood in the catheter and other medical device manufacturing arts. In one-embodiment, tubular body 152 is extruded from a biocompatible material such as TFE, having an inside diameter of approximately 0.09 inches and a wall thickness of about 0.01 inches.

The proximal end 154 of tubular body 152 is connected to a Y-adaptor 158. Y-adaptor 158 carries a control 160 for controlling the retrieval device as will be described. Control 160 in the illustrated embodiment comprises a thumb ring 162 which is slideably carried with respect to a pair of finger rings 164. Axial movement of the thumb ring 162 with respect to the finger rings 164 enlarges or retracts a retrieval loop 166 extending distally from distal end 156 of tubular body 152. Retrieval loop 166 is adapted to surround the inflated attenuator 66. In one embodiment, the loop 166 has an enlarged diameter of about 27 mm, and comprises a wire such as 0.016 inch diameter stainless steel cable wire.

In use, the loop 166 is opened once the distal end 156 of the tubular body 152 has reached the bladder. The loop 166 is positioned around the attenuator 66, and the proximal control 160 is manipulated to tighten the loop 166 around the attenuator 66. After the attenuator 66 has been securely grasped by the loop 166, a deflating tube 168, preferably having a sharpened distal tip 169 thereon, is distally advanced through the wall of the attenuator 66. Distal advancement of the deflating tube 168 may be accomplished by distally advancing a proximal control, such as control 172. The distal tip 169 is in fluid communication with a connector such as a standard luer adaptor 170 through a central lumen (not illustrated), so that an empty syringe or other device may be connected to the connector 170 and used to evacuate the contents of the ensnared attenuator 66. As the attenuator 66 is deflated, the control 160 may be manipulated to pull the collapsed attenuator 66 into the distal end 156 of the tubular body 152. The removal device 150 having the reduced attenuator 66 therein or carried thereby may be transurethrally removed from the patient.

Figure 21:
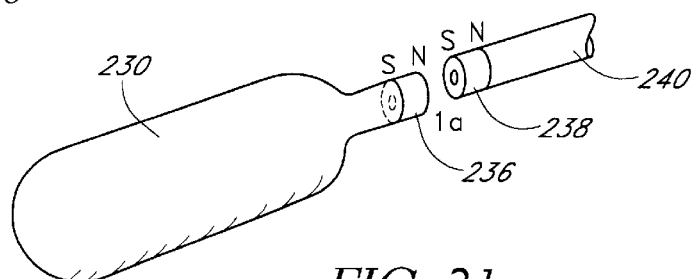
FIG. 21 is a schematic perspective view of the attenuator of FIG. 20, aligned with the distal end of a deployment or retrieval catheter.

A wide variety of modifications can be made to the foregoing removal device 150, within the spirit of the present invention. For example, the proximal controls 160 and 172 may be combined into a pistol grip or other configuration. Controller 172 or control 160 may additionally control deflection of the distal end 156 of the tubular body 152, or control rotation of the plane of the loop 166. In general, the removal device 150 preferably accomplishes the basic functions of enabling the location of the attenuator 66, capturing the attenuator, reducing the attenuator in size and removing the attenuator from the bladder. The capturing step may be accomplished by visualizing the attenuator through the urological cystoscope, or by "blind" techniques, such as the magnetic locator described in connection with FIGS. 21, 22, 23, below.

Referring to FIG. 13, there is illustrated a top plan view of an alternate attenuator 180 in accordance with the present invention. The attenuator 180 comprises an inflatable body 68 generally as has been described. An outer seam 78 may be provided with a valve 80. In this embodiment, an inner seam 182 defines a central region 184. The outer seam 78 and inner seam 182 define a generally torodial-shaped inflatable container 68. The central region 184 may comprise either a membrane or a central opening, depending upon the desired performance characteristics. The center hole may assist in the placement and location of the device within the bladder, permit additional baffling of the pressure waves within the bladder, minimize the attachment to the bladder wall by surface tension between the device and the bladder wall, and allow for urine flow through the hole in the event that the device is in or near the bladder neck.

Figure 14:
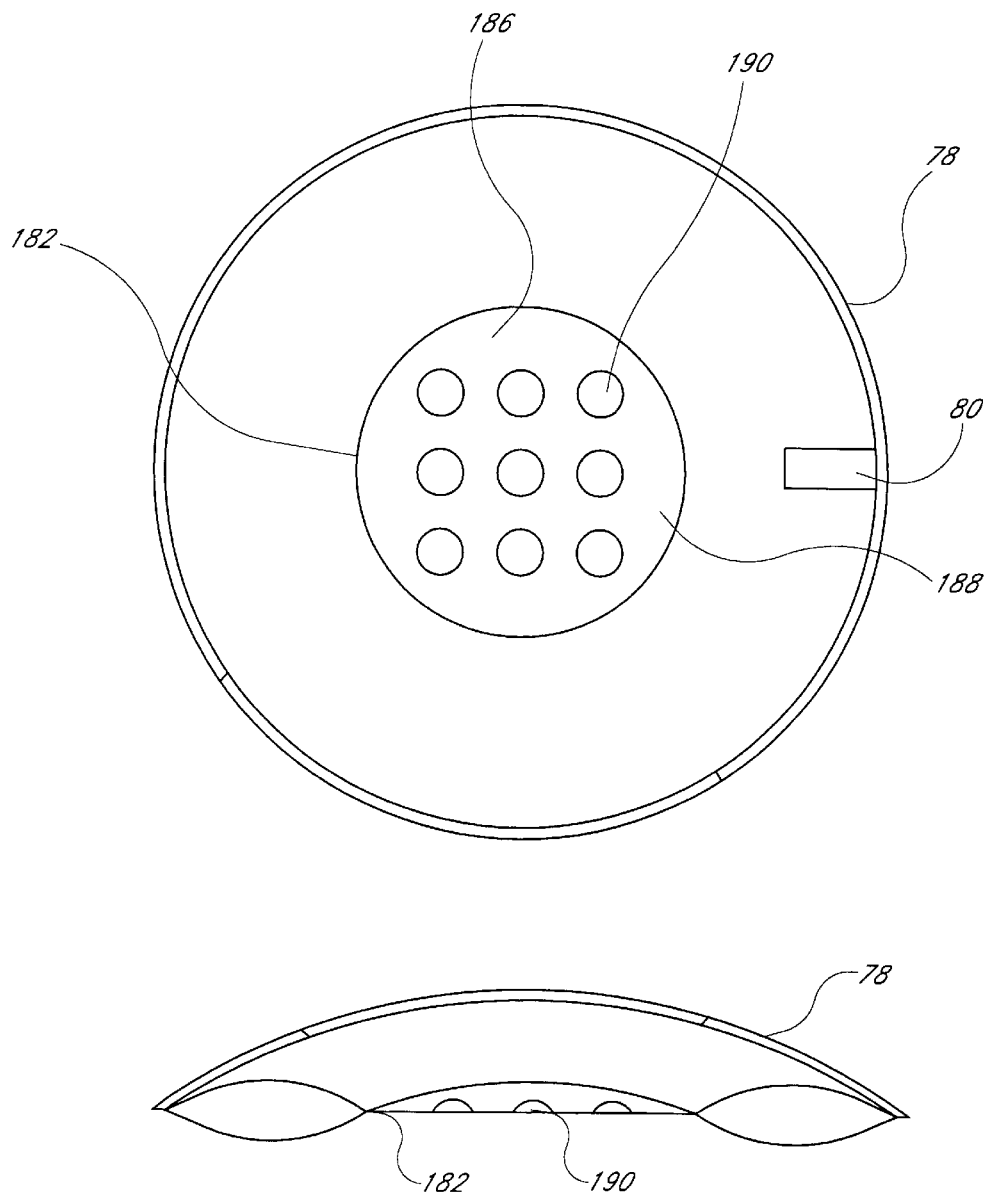
FIG. 14 is a schematic view of a toroidal shaped attenuator as in FIG. 13, with an integral baffle therein.

In one embodiment, illustrated in FIG. 14, the central region 184 comprises a baffle 186. The baffle 186 comprises a membrane 188 having a plurality of apertures 190 therein. In the illustrated embodiment, approximately nine round apertures 190 are provided, each having a diameter of about 0.2 inches. Generally at least about 9 apertures 190 are provided, and many embodiments include anywhere from about 1 to about 1000 apertures. The optimal number of apertures 190 and sum of the area of the apertures 190 compared to the total area of the baffle 186 may be optimized depending upon the desired performance characteristics. Apertures may have any of a variety of configurations, such as round holes, irregular openings, slits or others.

Figure 15:
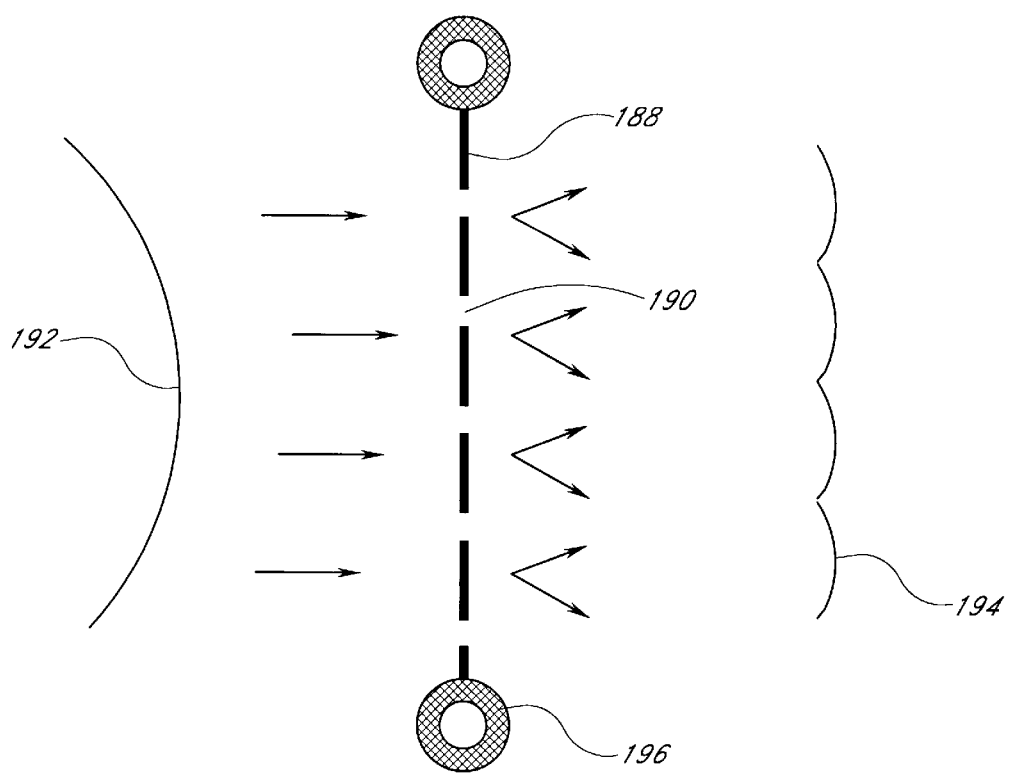
FIG. 15 is a schematic illustration of the attenuator disrupting the unitary progression of a pressure wavefront.

The wave diffuser function of the baffle 186 is schematically illustrated in FIG. 15. A wave front 192 may be generated by any of a wide variety of events, such as coughing, sneezing, laughing, physical movement, muscle spasms or others as is understood. Since urine comprises essentially non-compressible water, and due to the low dynamic compliance of the bladder the wave front 192 will propagate rapidly through the bladder to impact structures such as the trigone area and the urethra. Apparent transient pressure spikes as high as 80 cm $H_2O$ or greater can be experienced during normal activities. Because of the shape of the bladder, these pressure waves can in fact be focused onto the trigone and the bladder neck. In addition to reducing the pressure caused by pressure events such as coughing, the devices discussed above can also provide a baffle that distributes the wave across the bladder distributing and reducing the focused wave front that contacts the bladder neck.

If the attenuator 180, having a baffle 186 is positioned within the bladder, the baffle 186 functions to disrupt the unitary progression of the wavefront 192. The prediffusion wave front 192 is thus interrupted into a plurality of post-diffusion wave fronts 194 by the baffle 186. Although the sum of the resulting post-diffusion wave fronts 194 is essentially equal to the prediffusion wave front 192, the greater dispersion of force accomplished by the baffle 186 is believed by the inventors to reduce the apparent magnitude of the wave front 192 as experienced by target tissue within the bladder.

As will be apparent in view of the foregoing, the baffle 186 may be constructed in any of a variety of manners and still accomplish the intended result. Thus, although the attenuator 180 illustrated in FIGS. 13 and 14 comprises a generally toroidal-shaped inflatable container, any of a variety of other support structures may be utilized to maintain the baffle 186 in a useable configuration. The support 196 may alternatively comprise an inflatable tube, a resilient material such as nitinol wire, or other support structure as may be desired.

Figure 16:
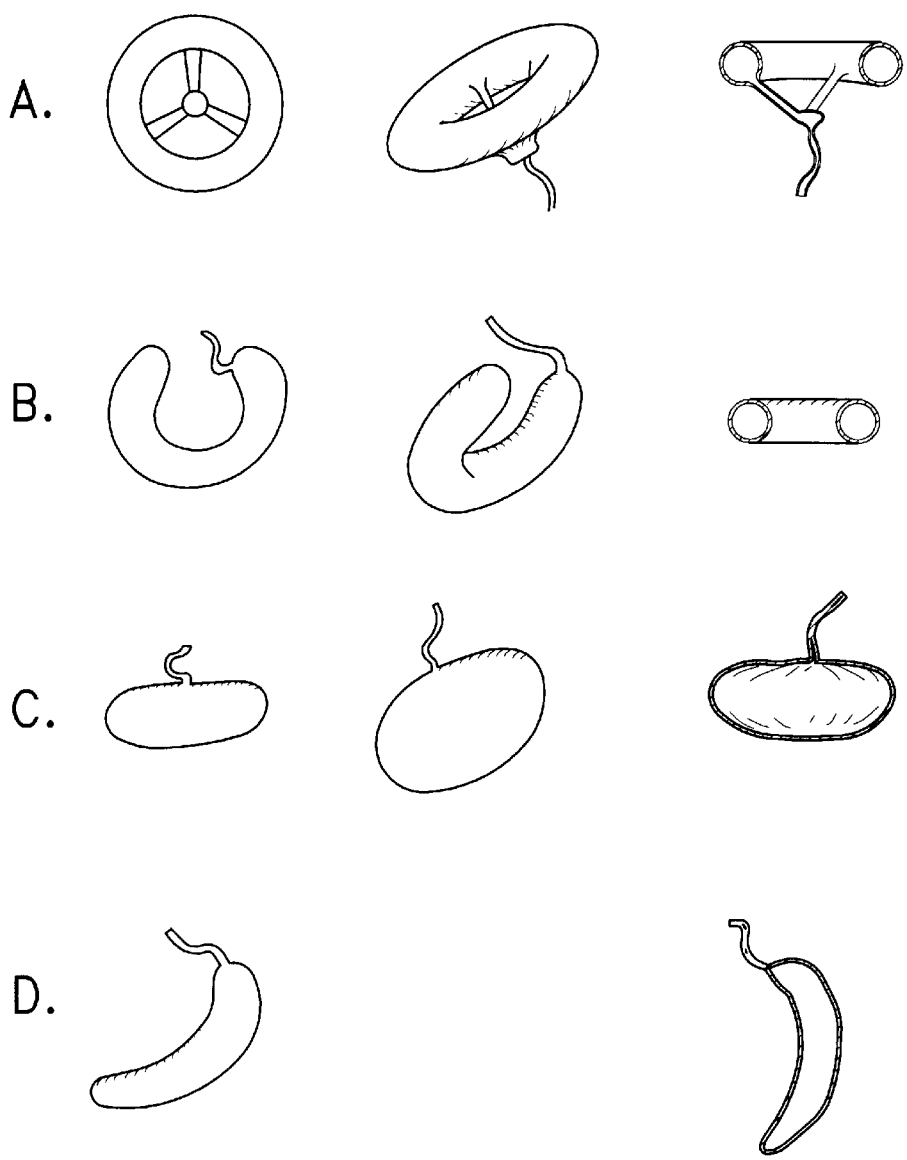
FIGS. 16A–D are schematic representations of a variety of inflatable attenuators in accordance with the present invention.

Referring to FIG. 16, there is illustrated a variety of alternative shapes for the attenuator 66, of the inflatable container variety. The devices used in embodiments of the present invention may take many shapes. In some instances it may be desirable for manufacturing purposes to have the shape resemble dip-molded devices like condoms, surgical glove fingers, or children's toys. However, many other forms may provide better performance, in particular for providing baffling of pressure waves as well as attenuation of pressure spikes. Possible shapes for the devices include torroid like shapes, similar in form but not size to donuts and inner tubes; spoked wheel forms; horseshoe-like forms; mushroom-like forms; and banana-like form.

In other embodiments of the present invention, the devices may be dip molded or extruded in a plurality of biocompatible materials. Furthermore, the devices may be fabricated from a variety of multi-layer composites or produced by a number of different manufacturing processes. The devices may also be formed made from thin film sheet stocks (mylar, polyethylene, polypropylene, polyurethane). It is important to note that the material does not need to be elastomeric at all for the invention to function. However, the materials chosen for use in embodiments of the present invention are to be sufficiently flexible in thickness as dictated by the selected designs. When the device is subjected to external pressures, the device material is able to transmit the pressure to the contained air or pressure management construct and respond sacrificially as one of the most compliant members of the urinary system.

FIG. 16A illustrates a toroidal embodiment, in which a plurality of central spokes are provided. FIG. 16B illustrates a crescent or "C" shaped attenuator. Any of a variety of spherical, oval, elliptical or other shapes may be utilized such as those illustrated in FIG. 16C, in which the greatest length dimension of the inflated attenuator is within the range of from about 1 to about 5 times the smallest cross-section. FIG. 16D illustrates a less arcuate variety as shown in FIG. 16B. In general, the attenuator 66 may take any of a variety of forms which provides a sufficient volume to achieve the desired attenuation function, and which will minimize or eliminate risk of loss or obstructing outflow through the urethra.

Figures 17A, 17B:
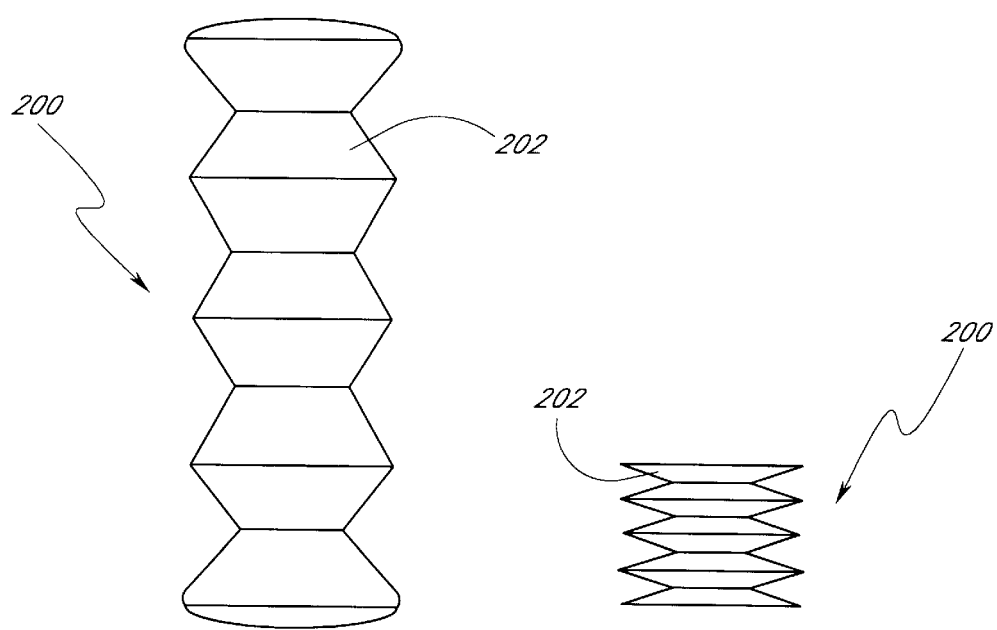
FIG. 17A is a side elevational schematic view of a bellows-type mechanically assisted accumulator in an expanded configuration.
FIG. 17B is a side elevational schematic view of the accumulator of FIG. 17a, in a compressed configuration to attenuate a pressure spike.

Referring to FIGS. 17A and 17B, there is illustrated an axially-compressible mechanical bellows type attenuator in accordance with the present invention. Devices of embodiments of the present invention for absorbing transient pressure changes include diaphragmatic structures, rigid structures both shape changing and rigid with a coating or a bellows or bellows-like device that can dampen pressure waves in an organ, chamber or cavity of the body as stand alone devices or as part of the wall or structure of the organ of interest. One embodiment of a mechanically assisted device is in FIG. 17. FIG. 17A is a mechanical bellows that is in a normally extended position. The pressure within the bellow is reduced such that the device normally retains its extended position, but will compress with external pressure exerted on the device. The bellow could be made from plastic or metal (such as titanium or stainless steel from Senior Flextronics, Inc. Sharon, Mass.). The bellow may be sealed, or covered in a material that allows for the reduction of air pressure within the device.

This approach has the advantage for significantly greater change of volume with change of pressure. The theoretical limits of the air cell described herein can only be reduced approximately 25% of its volume, but this bellows device can contract to almost 90% of its volume.

The bellow attenuator 200 comprises a membrane 202, which is collapsible in an accordion fashion. The membrane 202 may be self-supporting, or may be provided with an internal or external frame. The frame may comprise any of a variety of structures, such as a simple spring aligned in parallel with the longitudinal axis of the bellow, or pivotably moveable structures such as an axially compressible wire pantograph as will be understood in the art.

Figure 18:
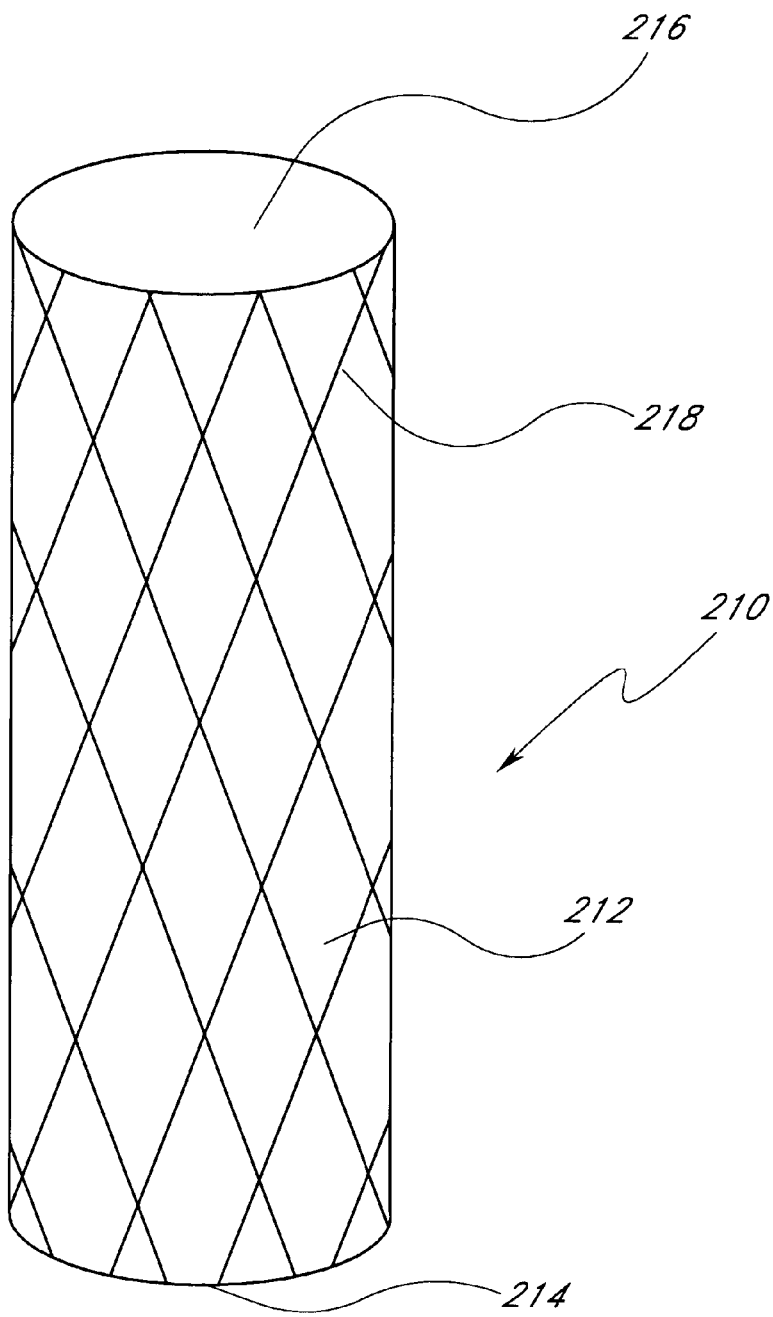
FIG. 18 is a side elevational schematic view of a self-expanding graft type mechanically assisted accumulator.

Referring to FIG. 18, there is illustrated an alternative mechanically-assisted accumulator 210 in accordance with the present invention. In this embodiment, a compressible tubular wall 212 having closed ends 214, 216 is supported by a self-expanding tubular frame 218. Any of a variety of self-expanding tubular or spherical frame structures may be utilized, such as "zigzag" wire frames well known in the abdominal aortic aneurysm graft arts. Although the abdominal aortic aneurysm graft application generally requires a relatively high, radially outwardly directed force, the present application would preferably be compressible with a relatively low compressive force (i.e., low radial force). This may be accomplished by using wires of smaller gauge, less wire per graft, leaving adjacent apexes unconnected to each other, or other technique to reduce the radial force of the wire cage. The wire cage or other support structure is preferably surrounded by a water impermeable membrane such as a balloon. Pressure within such balloon may be lower than 1 atm.

Figure 19A:
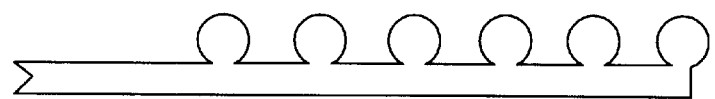
FIG. 19A is a side elevational schematic view of a multiple chamber attenuator in accordance with a further aspect of the present invention.
Figure 19B:
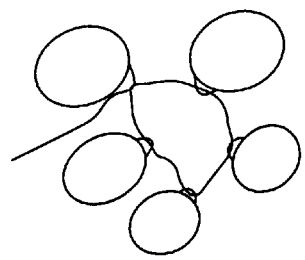
FIG. 19B is a schematic illustration of the multiple chamber attenuator of FIG. 19A, in a deployed orientation to ensure retention within the bladder.

Referring to FIG. 19, there is illustrated an alternative layout for the inflatable attenuator 66 of the present invention. In this embodiment, a plurality of attenuators are connected by a common flow path, so that the plurality of attenuators can be inflated through a single fill port. Alternatively, a plurality of self-expanding attenuators are connected by a suture, Nitinol wire, or other tether. This embodiment may allow minimizing the crossing profile, or maintaining a constant crossing profile for an attenuator of any desired total inflated volume.

FIGS. 20–23 illustrate a magnetic locating system for enabling "blind" retrieval without the use of a cystoscope. To remove the attenuator from the bladder, the retrieval assembly is inserted into the urethra for intravesical capture, deflation, and extraction of the attenuator. The retrieval assembly utilizes a magnet whose polarity and flux path is oriented in a manner to ensure predictable attraction and coupling of a magnet-containing attenuator to the retrieval assembly. The retrieval assembly is coupled back to the attenuator, and the attenuator may be punctured and deflated using the jaws of biopsy-like forceps (or other solution suitable for deconstructing the device) located at the distal end of the retrieval assembly. Alternatively, residual gas may be passively vented into the bladder or through the retriever body. Once deflated the attenuator may be withdrawn through the urethra attached to the retrieval assembly or allowed to pass out of the bladder as part of the urine flow.

Thus, referring to 20, there is illustrated an attenuator 230 such as an inflatable balloon as has been described previously herein. The attenuator 230 is provided with a valve 232 and a locating element 234. Locating element 234 may be any of the variety of structures which enable location of the attenuator 230, preferably without the need for direct visualization.

Figure 22:
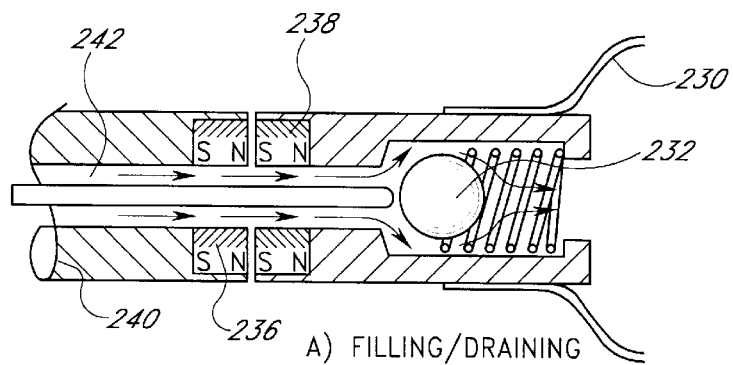
FIG. 22 is a fragmentary cross-sectional view through the distal end of a deployment or retrieval catheter, and the proximal end of the valve on an attenuator, illustrating the valve in a filling or draining orientation.
Figure 23:
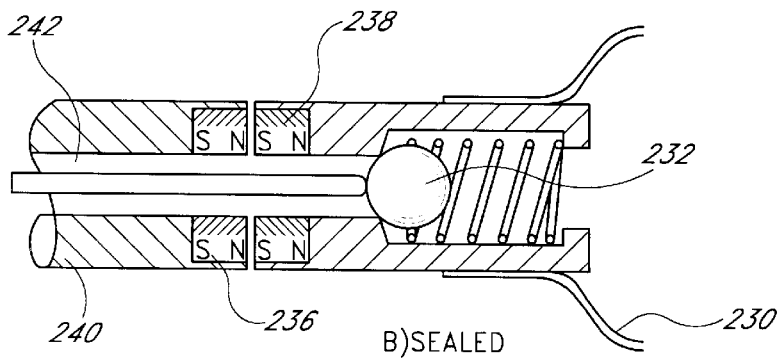
FIG. 23 is a fragmentary cross-section as in FIG. 22, showing the valve in a sealed orientation.

In the illustrated embodiment, the locating element 234 is one or more magnets 236. In the embodiment illustrated in FIG. 21, the magnet 236 comprises an annular ring, for surrounding the flow path 83. A corresponding magnet 238 having reversed polarities from the polarity of the magnet 236 is provided on the distal end of a catheter 240. The attractive forces of the opposing polarity magnets 236 and 238 will cause the catheter 240 to couple on to the attenuator 230, as illustrated in FIG. 22, when the catheter 240 is positioned in the vicinity of the attenuator 230.

Figure 20:
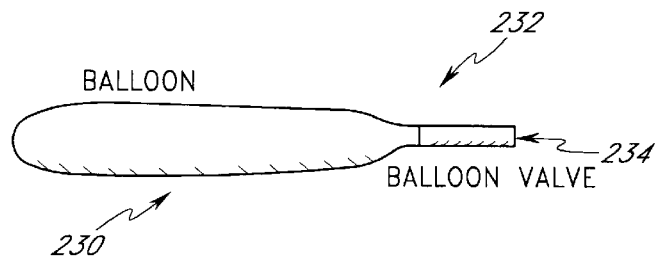
FIG. 20 is a side elevational schematic view of an inflatable balloon-type attenuator, having a locatable balloon valve thereon.

Referring to FIG. 20, at least one lumen 242 places the attenuator 230 in fluid communication with the catheter 240 when the locating element 234 is coupled to the catheter 240. This lumen 242 may be utilized to either introduce inflation media or remove inflation media from the attenuator 230. In FIG. 22, the valve 232 is a ball valve, which is biased in the closed orientation. However, the mechanism and structures disclosed herein may be used on any of the other valves disclosed elsewhere herein. As illustrated in FIG. 22, a valve actuator 234 may be advanced distally 9, through the lumen 242 to displace the valve 232 and enable infusion or removal of inflation media. Following the desired volume of infusion or removal of inflation media, the valve actuator 234 may be proximally retracted, to enable the valve to close under its own bias. See FIG. 23.

The opposing magnets 236 and 238 may be utilized solely as a locating structure, such that an additional locking element (not illustrated) may be utilized to lock the catheter 240 on to the attenuator 230. This may be desirable if the strength of the bond formed between the two magnets is insufficient to keep the attenuator 230 coupled to the catheter 240 during the filling or removal steps. In addition, following deflation of the attenuator 230, the catheter 240 will generally require a relatively strong coupling to the attenuator 230 to retrieve the attenuator 230, as will be apparent to those of skill in the art in view of the disclosure herein.

In accordance with another embodiment of the present invention, the retrieval catheter is provided with one or more ultrasound transducers near a distal end thereof. An air filled attenuator should strongly reflect an ultrasound signal, in a manner similar to the reflection achieved at an air-water interface. A retrieval catheter provided with a deflectable distal tip and ultrasonic capabilities should be able to navigate through the bladder to locate an attenuator without the need for visualization. The retrieval catheter may additionally be provided with a grasping element, such as two or more opposing mechanical graspers, and/or a vacuum lumen, for attaching to the surface of the attenuator using suction. Once attached, the attenuator can be pierced and transurethrally withdrawn.

In other embodiments of the present invention, devices may assume multiple shapes during the course of their use. For example, the device may be completely deflated for introduction and inflated to varying degrees after introduction. The device may be adjusted through the inflation/deflation of secondary or multiple containment cells for such purposes as ballasting or the addition of a diagnostic, therapeutic or signaling substance. This may occur through multiple uses of a single, or single uses of a multi lumen, multi ported structure or combinations thereof.

In other embodiments of the present invention, the fill tube/introducer assembly and the retrieval assembly are two separate instruments.

In other embodiments of the present invention, the fill tube/introducer assembly and the retrieval assembly may be implemented using a single instrument. Alternatively, one instrument may be used having different distal ends for the fill tube/introducer assembly and the retrieval assembly.

In other embodiments of the present invention an endoscope may be used to launch and retrieve the device.

In other embodiments of the present invention the distal tip of the fill tube/introducer may be straight, pre-curved, malleable, or steerable (e.g., by pull wires) in order to facilitate delivery and/or release of the device.

In other embodiments of the present invention the separation of the device from the fill tube may be accomplished using the wall of the urethra or neck of the bladder as a mechanically resistant body.

In other embodiments of the present invention the fill tube and introducer may consist of a single tubular element, a series of concentric tubular elements, a series of non-concentric tubular elements, an extruded element, a spirally wound guidewire element, or any combination of the aforementioned elements arranged in a manner to provide the desired functions.

In other embodiments of the present invention irritation concerns are addressed through the use of coatings to physically or chemically modify the device in whole or part in order to modulate characteristics such as lubricity and the ability to inhibit the deposition of materials present in the urinary tract. For example, substances such as sulfated polysaccharides may be used before, during or after introduction to the patient. In addition the use of a plurality of construction materials with unique surface properties may also be used for this purpose.

In other embodiments of the present invention the device may also include a portal that spans the distance from the internal aspect to the external aspect that allows for the location of an erodable substance that would allow for the deflation or deconstruction of the device after exposure to urinary tract conditions for a prescribed period of time. This approach may also be used for the programmed bolus release of single or multiple therapeutic, diagnostic or signaling substances from single or multiple chambers within the device.

In other embodiments of the present invention the device may be equipped with a valve/port that is programmable, self-regulating or responsive to stimuli, which may or may not be physiological. Telemetry, physical connection or remote signaling may be used to elicit a desired response.

In other embodiments of the present invention the device will be capable of accepting, capturing, translating physical forces within the urinary tract to energize a site within the device for the positive displacement of substances outside the boundary of the device in either continuous or bolus presentation.

In other embodiments of the present invention the device port/valve need not be associated with the sealing edge of the device.

Figure 24:
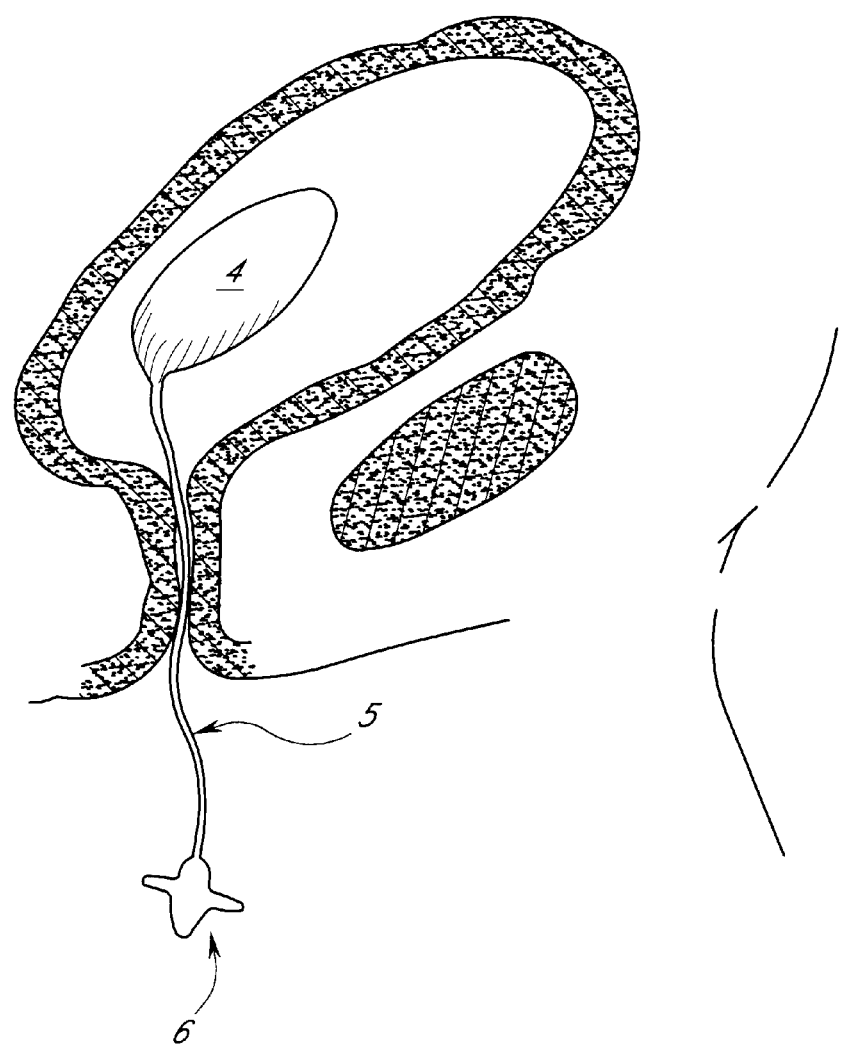
FIG. 24 is a schematic cross-section through a bladder, showing an attenuator therein, having an attached, external tether.
Figure 25:
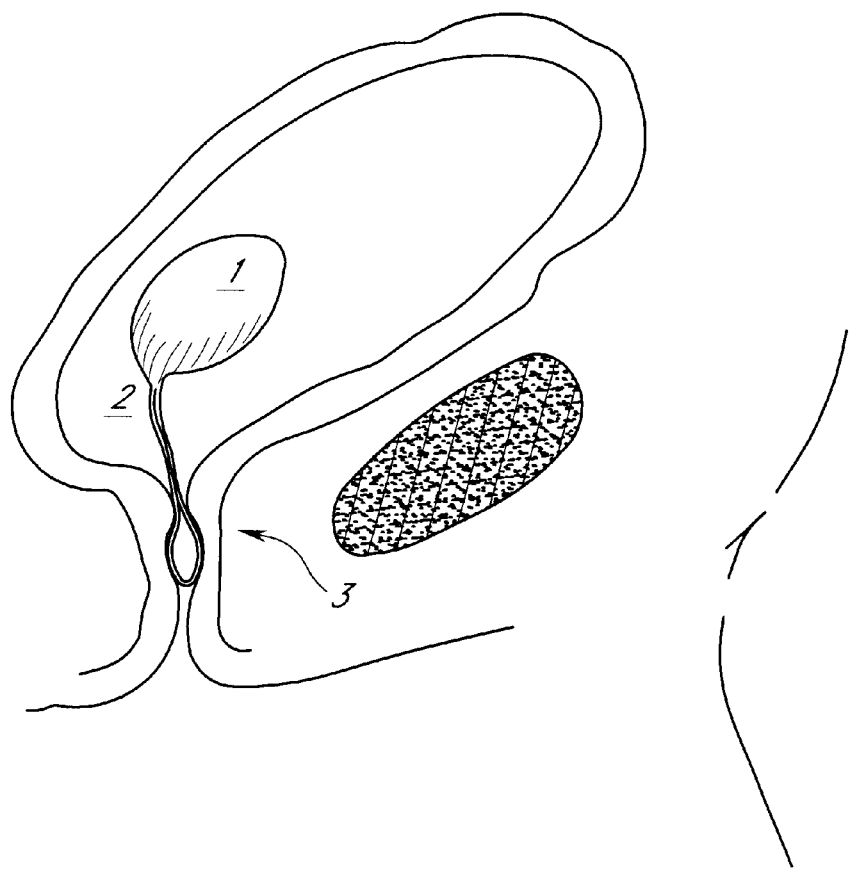
FIG. 25 is a schematic cross-section through a bladder, showing a two-component attenuator in which a primary compressible component is positioned within the bladder and a secondary inflatable component is positioned within the urethra.
Figure 26:
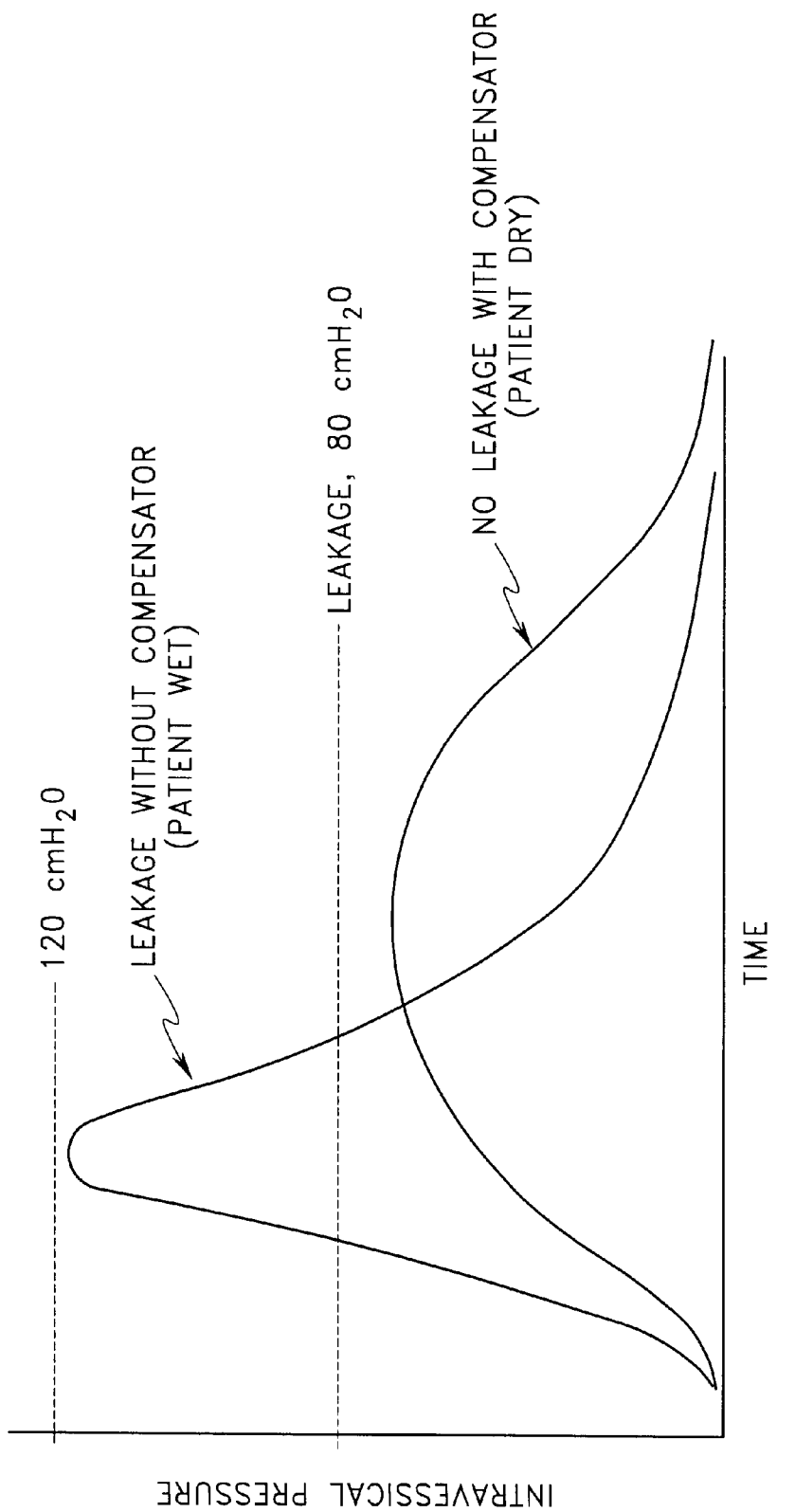
FIG. 26 illustrates the effect on intravesical pressure of the presence of an implanted attenuator in accordance with the present invention.
Figure 27:
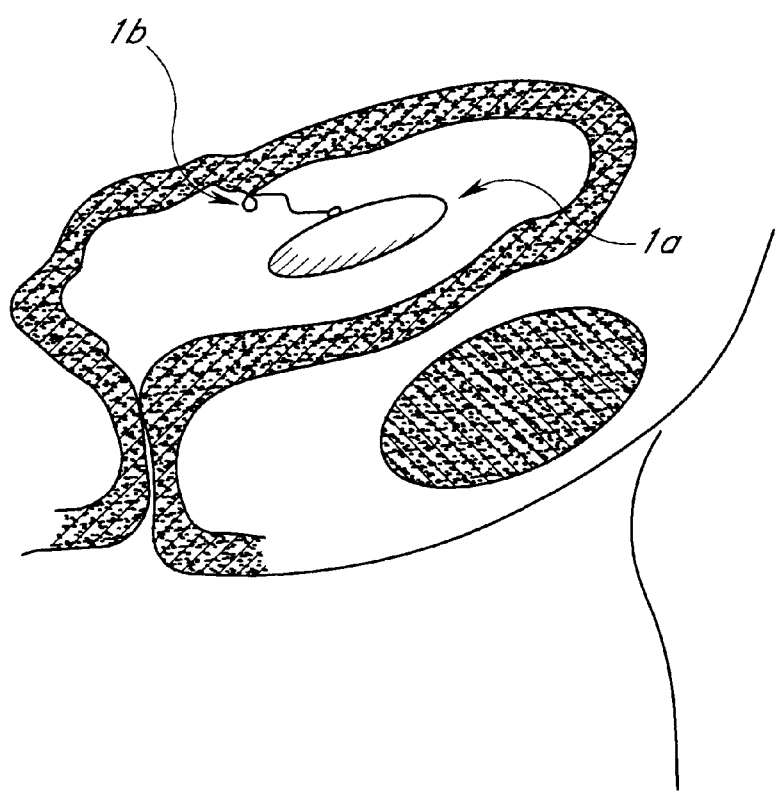
FIG. 27 is a schematic cross-sectional view through a bladder, showing an attenuator anchored to the bladder wall.
Figure 28:
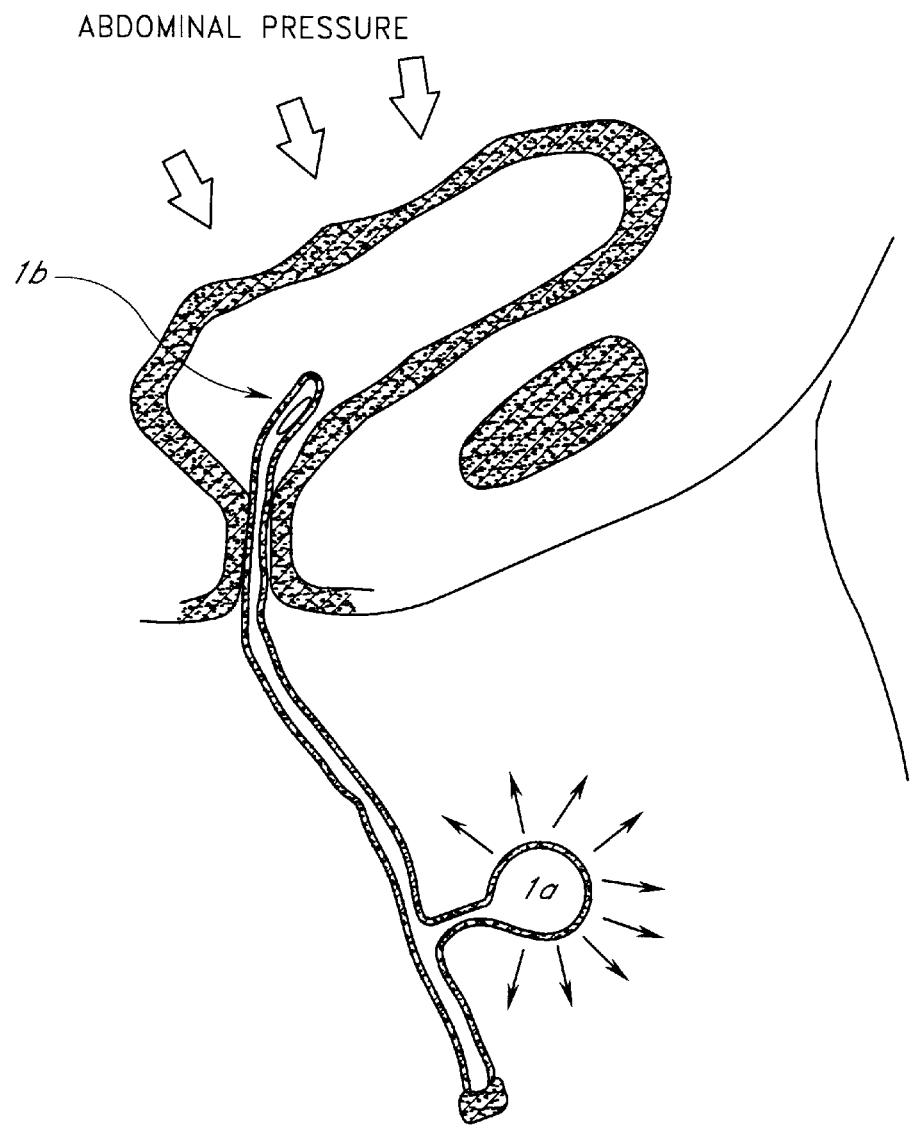
FIG. 28 is a schematic cross-sectional view showing a bladder, and the transurethral placement of a dynamic compliancy measurement catheter in accordance with the present invention.

Other embodiments of the present invention includes a device similar to the other described embodiments, however including a thin, pliable safety tether long enough to extend from the device and exit from the meatus. See FIG. 24. The tether can be constructed of accepted materials such as those used in the manufacture of sutures, catheters and may also possess anti-microbial properties. In one embodiment, the distal end of the tether may be terminated with a lightweight pendant of sufficient bulk to prevent ingress of the entire tether into the urethra. During normal use, the pendant may be temporarily affixed to the patient's pelvic region. The tether may be used to remove or deconstruct the device, and the tether provides the patient with the capability of instant removal of the device in the event the patient feels compelled to extract the device.

Other embodiments of the present invention are similar to those described above, except that the device is a chambered structure consisting of multiple subchambers for multiple functions. See FIGS. 25 and 25A–C. The primary device may or may not be fluidically connected to the secondary device. The fluidic connection also acts as a tether with sufficient service loop to allow the secondary device to be placed into the urethra while the primary device remains untethered in the bladder. During a urinary pressure spike, gas within the primary device compresses proportionally with the external load. The compressed gas is then allowed to transfer to the secondary device, dwelling in the urethra, and causing a proportional expansion of the secondary device. The design of the secondary device directs expansion in an outward radial direction, transverse to the longitudinal axis of the urethra, thus augmenting the natural inward radial contraction of the urethra. This type of "on demand" synchronous resistance augmentation may be much more effective than other forms of passive or patient controlled augmentation devices. Another benefit of this embodiment of the present invention is that the synchronous outward radial forces may help to positionally stabilize the device within the urethra. Passive devices must maintain a constant retention capability (force or displacement of tissue) sufficient to resist the maximum expulsion forces at all times. This level of retention may lead to patient discomfort and cause long-term tissue damage.

In other embodiments of the present invention, the primary device may resemble a small three-spoked automotive steering wheel, or a rotating toroidal space station. See FIG. 16A. The outer ring would contain the primary device; the inwardly radiating spokes would provide fluid conduits and mechanical support for the secondary device attachment. The primary device may also incorporate one or more shape holding super elastic wire members to aid in positional stability of the primary device. The secondary device could resemble the distal tip section of a small diameter angioplasty device and be affixed to the central hub.

In other embodiments of the present invention, a secondary device inflation/deflation response can be design regulated if desired. For example, it may be beneficial to inflate the secondary as quickly as possible, but induce a response lag in the deflation/inflation cycle to protect against a second cough, sneeze or jumping jack.

In other embodiments of the present invention, a pressure compensator or bladder trainer may be implanted within the abdominal cavity and be hydraulically or pneumatically connected to the bladder or be installed as a component of the bladder wall. The device would be constructed of a rigid external enclosure to shield the compressible elements from abdominal forces. The function of this embodiment would be not only to manage the transvessicular pressure in treatment of a clinical complaint, but also to introduce pressure waves either outside or inside the bladder in order to increase the muscle tone, compliance or affect the neuromuscular elements of the bladder.

The embodiments described above have been described for use in human bladders. As understood by those skilled in the art, the present invention is not limited to human use, but appropriately scaled versions of the inventions disclosed here may also provide clinical benefits to other animals including mammalian household pets.

Embodiments of the present invention provide significant advantages over prior art devices. These advantages include: significant reductions in bladder dysfunction related events; the ability to retrain a bladder with other than normal compliance; no patient interaction required to operate or maintain the device; patient is allowed to void in a normal fashion; no infection conduit between the bladder and the distal end of the meatus; minimal sensation generated by the device; low cost to manufacture; cost effective solution for patient when compared to existing treatments; and ease of installation and removal for clinician.

The present invention also provides devices and methods for measuring the dynamic compliance of the bladder. In one embodiment, a device can be used in combination with the fill tube/introducer to measure the dynamic compliance of the bladder. One lumen of the fill tube can be used to rapidly inflate the device, while pressure measurements of the bladder are made via a second lumen. In one embodiment, the volume is expanded by at least about 30 cc or 50 cc up to as much as 200 cc in a time period of from about 0.5 seconds to 10 seconds to measure the dynamic compliance of the bladder.

The present invention provides methods and devices for the restoration of dynamic compliance of the bladder by retraining the bladder tissue by introducing pressure waves at a prescribed place and with prescribed characteristics.

The present invention also provide methods and devices for the programmatic delivery of clinical therapeutics in association with defined pressure events. The present invention could be added to other intravesical devices, such as Foley catheters, intravesical infusers, such as those described in WO 99/24106, or the ends of urethral stents to facilitate delivery, to treat multiple symptoms, or to enhance the performance of either device.

For example, the attenuator could work in combination with intravesical infusers, to time the release of medications relative to pressure events within the bladder.

The present invention also provides an atraumatic method of measuring intravesical pressure without the need for any external connection by placing a pressure transducer and telemetry device within the accumulator. This secures the transducer within the bladder and prevents the need to attach the transducer to the bladder wall.

Embodiments of the present invention are not limited to intravesical devices, but also include devices and methods for controlling pressure transients in other organs of the body, as will now be discussed.

Figure 29:
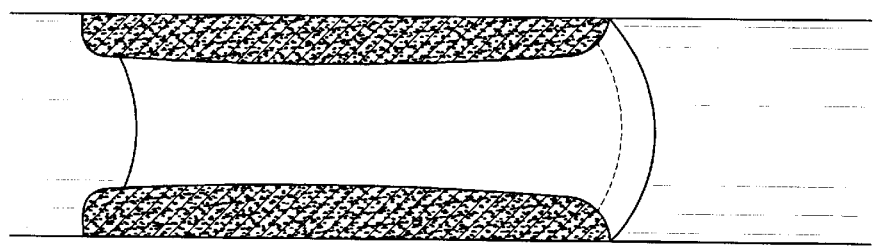
FIG. 29 is a schematic cross-sectional view through a vessel, illustrating a tubular attenuator therein.
Figure 30A:
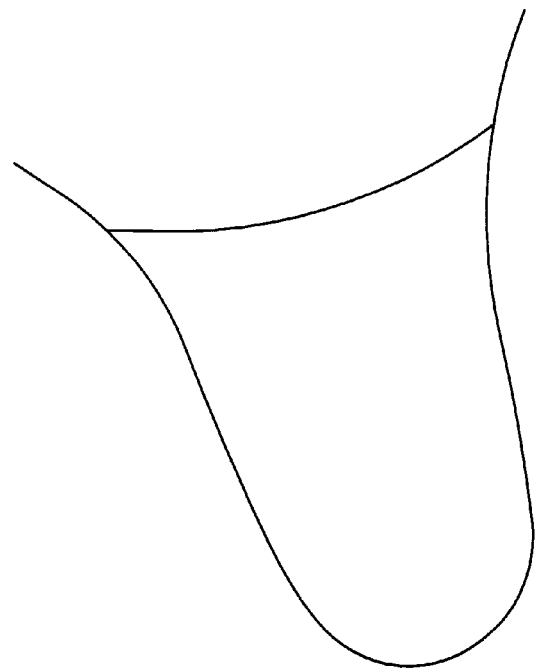
FIG. 30A is a schematic cross-section of a left atrial appendage of the heart, having an air cell attenuator positioned therein.
Figure 30B:
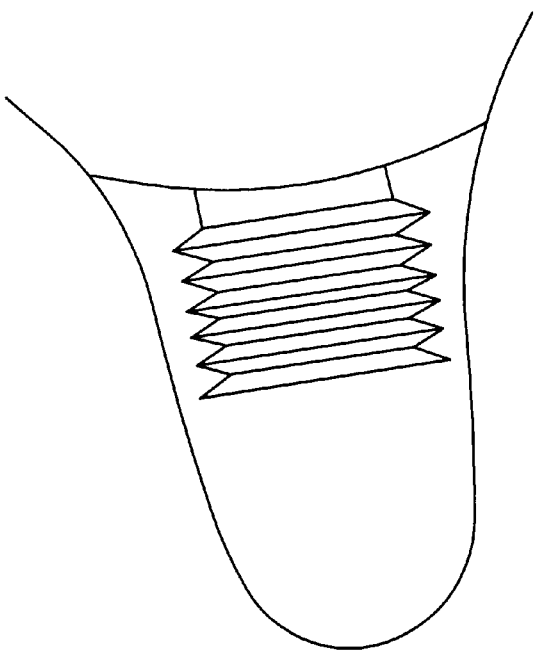
FIG. 30B is a schematic cross-section as in 30A, showing a bellows-type attenuator positioned in the left atrial appendage.

One embodiment of the present invention is intended for use in cardiovascular applications to modulate pressure waves to protect the heart and/or the vasculature from being damaged due to exposure to the pulsitile forces of normal or extreme physiological events by reducing mean arterial pressure, systolic pressure and or diastolic pressure. See FIG. 29. An accumulator can be placed in the wall of the heart, within a major artery, or within the left atrial appendage of the heart (see FIGS. 30A and 30B) to reduce risk of renal failure, stroke, heart attack, blindness. An accumulator can be placed on or within the right side of the heart or in a pulmonary artery to reduce symptoms of primary permanent hypertension. An accumulator can also be placed on the venous side of the vasculature system, such as within the wall of the vena cava or attached to a Greenfield filter within the vena cava to prevent portal hypertension and/or esophageal varicies. An accumulator, such as an air cell, can be attached to or encompass a stent for placement within the vasculature.

Figure 31:
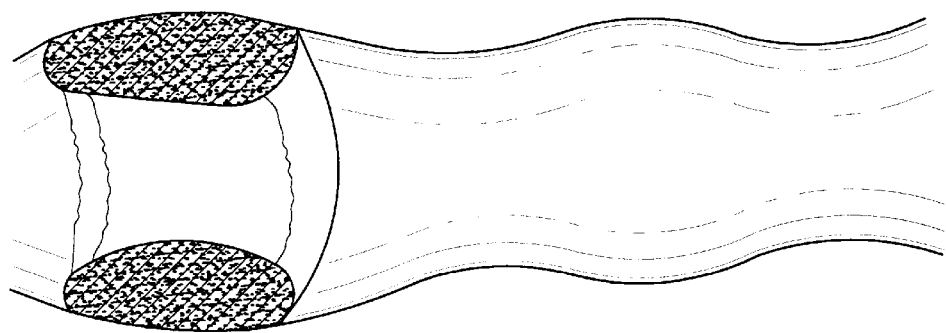
FIG. 31 is a schematic cross-section of a tubular attenuator positioned within the colon.

Another embodiment of the present invention may also be used in the gall bladder to modulate pressure contained therein. Pressure in the gall bladder may lead to undesired events such as the formation of stones or pain for the patient. An accumulator can also be placed in the esophagus on the end of an NG tube to limit spasm. An accumulator can be placed in the bowel to treat irritable bowel syndrome, minimize crons disease, cramping, or any other disorder resulting from peristalsis. See FIG. 31.

Another embodiment of the present invention may also be used in the field of opthaniology to support cranio-facial tissue during healing after a traumatic event or intraoptically as therapy for acute angle closure glaucoma.

Another embodiment of the present invention may also be used in the field of orthopedics as an implantable or external device to protect against pressure waves and control the location of a healing bone after a traumatic event.

Another embodiment of the present invention may also be used in the field of otorhinolaryngology for the management of pressure waves in the sinus cavities, including in and around the ears, the nose and the throat.

An accumulator can also be placed in the lung to treat disorders such as asthma, bronchio spasms or prevent damage from coughing in fragile lung tissues in emphysema sufferers, for example.

An accumulator can also prevent CNS problems such as head trauma, cerebral edema, and hydrocephalus. The accumulator could be placed in the epidural pocket under the skull.

In embodiments of the present invention described above, air cell-like devices are placed in the bladder and/or other organs of the body and filled with or consisting of a compressible substance to provide pressure compensation. Additionally, active, programmable pressure compensators or generators are described designed to monitor pressure events, respond in a predetermined fashion, and record or transmit that information outside the body. Additionally, a reliable, maintenance-free therapeutic delivery system is described designed to programmatically release or distribute an agent into an organ of the body using an erodable or deformable support matrix or material of construction, and/or a programmable or responsive valving system.

Having thus described certain embodiments of the present invention, various alterations, modifications and improvements will be apparent to those of ordinary skill in the art. Such alterations, variations and improvements are intended to be within the spirit and scope of the present invention. Accordingly, the foregoing description is by way of example and is not intended to be limiting.

What is claimed is:

1. A method of attenuating or deflecting pressure in an anatomical structure, comprising placing an attenuator in communication with a body cavity, exposing the attenuator to an increase in pressure within the cavity, and attenuating the increased pressure.

2. A method of attenuating pressure in an anatomical structure as in claim 1, wherein the placing step comprises placing the attenuator within the cavity.

3. A method of attenuating pressure in an anatomical structure as in claim 2, wherein the cavity is within the bladder.

4. A method of attenuating pressure in an anatomical structure as in claim 2, wherein the cavity is in communication with the cardiovascular system.

5. A method of attenuating pressure in an anatomical structure as in claim 1, wherein the attenuation is accomplished by a reduction in volume of the attenuator.

6. A method of attenuating pressure in an anatomical structure as in claim 5, wherein the reduction in volume is responsive to the increase in pressure.

7. A method of attenuating pressure in an anatomical structure as in claim 2, wherein the attenuator comprises a compressible wall.

8. A method of treating urinary tract dysfunction, comprising the steps of:
identifying a patient exhibiting symptoms of incontinence; and
positioning a compressible pressure attenuator in the patient's bladder.

9. A method of treating urinary tract dysfunction as in claim 8, wherein the positioning step comprises carrying the attenuator transurethrally on a deployment device.

10. A method of treating urinary tract dysfunction as in claim 8, further comprising the step of removing the attenuator from the bladder.

11. A method of treating urinary tract dysfunction as in claim 8, wherein the attenuator maintains the intravesical pressure below the urethral leak point pressure.

12. A method of treating urinary tract dysfunction as in claim 8, wherein an intravesical pressure spike which would have been at least about 60 cm $H_2O$ without the attenuator is maintained by the attenuator at no more than about 40 cm $H_2O$.

13. A method of treating urinary tract dysfunction as in claim 12, wherein an intravesical pressure spike which would have been at least about 80 cm $H_2O$ without the attenuator is maintained by the attenuator at no more than about 50 cm $H_2O$.

14. A method of treating urinary tract dysfunction as in claim 13, wherein an intravesical pressure spike which would have been at least about 120 cm $H_2O$ without the attenuator is maintained by the attenuator at no more than about 60 cm $H_2O$.

15. A method of treating urinary tract dysfunction comprising advancing a compressible device transurethrally into the bladder, wherein the device comprises a wire frame.

16. A device for treating urinary tract dysfunction, comprising a compressible attenuator having an expanded volume within the range of from about 1 cc to about 200 cc, which is compressible to no more than about 80% of its expanded volume under a pressure of about 80 cm $H_2O$.

17. A device as in claim 16, comprising an inflatable balloon.

18. A device as in claim 16, comprising a compressible bellow.

19. A device as in claim 16, further comprising a pressure transducer.

20. A device as in claim 17, further comprising an inflation port.

21. A device as in claim 20, further comprising a valve in communication with the inflation port.

22. A method of treating a patient, comprising the steps of:
providing a compressible attenuator which is moveable from a first, introduction configuration to a second, implanted configuration;
introducing the attenuator into the body while in the first configuration;
transforming the attenuator within the body to the second configuration; and
attenuating a pressure spike within the body by reversibly reducing the volume of the attenuator in response to the pressure spike.

23. A method as in claim 22, wherein the introducing step comprises transurethrally introducing the attenuator into the bladder.

24. A method as in claim 22, wherein the transforming step comprises at least partially inflating the attenuator.

25. A method as in claim 22, wherein the transforming step comprises permitting the attenuator to transform under its own bias.

26. A method as in claim 22, wherein the attenuating step comprises reducing the volume of the attenuator by at least about 5%.

27. A method as in claim 22, wherein the attenuating step comprises reducing the volume of the attenuator by at least about 10%.

28. A method as in claim 22, wherein the attenuating step comprises reducing the volume of the attenuator by at least about 25%.

29. A method as in claim 22, further comprising the step of removing the attenuator from the body.

30. A method of estimating the dynamic compliance of the bladder, comprising the steps of infusing a volume of fluid into the bladder and measuring the intravesical pressure in the bladder.

31. A method of estimating the dynamic compliance as in claim 30, wherein the infusing step comprises infusing a volume of at least about 50 ccs over a time of no more than about 10 seconds.

32. A method of estimating the dynamic compliance as in claim 30, wherein the infusing step is accomplished through a first lumen of a catheter, and the measuring step is accomplished through a second lumen of the catheter.

33. An attenuator, for attenuating pressure variations in an anatomical structure, comprising a moveable wall which defines a displacement volume, in which at least a portion of the wall is moveable between a first displacement volume for placement within the anatomical structure, and a second, enlarged displacement volume for attenuating pressure changes within the structure, and a fuse for enabling the attenuator to change from the second displacement volume to a reduced displacement volume for removal of the attenuator from the anatomical structure.

34. An attenuator as in claim 33, wherein the fuse enables an automatic reduction in the displacement volume following a treatment period.

35. An attenuator as in claim 34, wherein the fuse comprises an absorbable material.

36. An attenuator as in claim 35, wherein the fuse comprises the entire wall.

37. An attenuator as in claim 35, wherein the fuse comprises a portion of the wall.

38. An attenuator as in claim 35, wherein the fuse comprises a seam in the wall.

39. An attenuator as in claim 35, wherein the fuse is carried by the attenuator.

40. An attenuator as in claim 35, wherein the fuse comprises at least a portion of a valve.

41. A method of treating urinary tract dysfunction, comprising the steps of positioning an attenuator within the bladder, wherein the attenuator remains in the bladder for a treatment period, changes in form following the treatment period, and is transurethrally expelled from the bladder following the change in form.

42. A method of treating urinary tract dysfunction as in claim 41, wherein the treatment period is at least about 15 days.

43. A method of treating urinary tract dysfunction as in claim 41, wherein the treatment period is at least about 30 days.

44. A method of treating urinary tract dysfunction as in claim 41, wherein the changing in form step comprises deflating.

45. A method of treating urinary tract dysfunction as in claim 41, wherein the changing in form step comprises at least partially dissolving.

46. A method of treating urinary tract dysfunction as in claim 41, wherein the changing in form step comprises reducing in volume.

47. A method as in claim 5, wherein the attenuating step comprises reducing the volume of the attenuator by at least about 5%.

48. A method as in claim 5, wherein the attenuating step comprises reducing the volume of the attenuator by at least about 10%.

49. A method as in claim 5, wherein the attenuating step comprises reducing the volume of the attenuator by at least about 25%.

50. A method as in claim 3, wherein the attenuator maintains the intravesical pressure below the urethral leak point pressure.

51. A method as in claim 50, wherein an intravesical pressure spike which would have been at least about 60 cm $H_2O$ without the attenuator is maintained by the attenuator at no more than about 40 cm $H_2O$.

52. A method as in claim 50, wherein an intravesical pressure spike which would have been at least about 80 cm $H_2O$ without the attenuator is maintained by the attenuator at no more than about 50 cm $H_2O$.

53. A method as in claim 50, wherein an intravesical pressure spike which would have been at least about 120 cm $H_2O$ without the attenuator is maintained by the attenuator at no more than about 60 cm $H_2O$.

54. A method as in claim 1, wherein the placing step comprises carrying the attenuator transurethrally on a deployment device.

55. A method as in claim 54, wherein the attenuator comprises a compressible container.

56. A method as in claim 54, further comprising the step of removing the attenuator from the bladder.

57. A method as in claim 3, further comprising the steps of leaving the attenuator in the bladder for a treatment period, wherein the attenuator changes in form following the treatment period, and is transurethrally expelled from the bladder following the change in form.

58. A method as in claim 57, wherein the treatment period is at least about 15 days.

59. A method as in claim 57, wherein the treatment period is at least about 30 days.

60. A method as in claim 57, wherein the changing in form step comprises deflating.

61. A method as in claim 57, wherein the changing in form step comprises at least partially dissolving.

62. A method as in claim 57, wherein the changing in form step comprises reducing in volume.

* * * * *